United States Patent
Zhou et al.

(10) Patent No.: US 6,610,781 B1
(45) Date of Patent: Aug. 26, 2003

(54) REINFORCED NETWORKED POLYMER/CLAY ALLOY COMPOSITE

(75) Inventors: Zhihong Zhou, Edmonton (CA); John Donald Payzant, Edmonton (CA); Walter Van Woudenberg, Greenwood Village, CO (US)

(73) Assignees: Alberta Research Council Inc., Edmonton (CA); Nilex, Inc., Edmonton (CA)

( * ) Notice: Subject to any disclaimer, the term of this patent is extended or adjusted under 35 U.S.C. 154(b) by 0 days.

(21) Appl. No.: 09/579,701

(22) Filed: May 26, 2000

Related U.S. Application Data

(63) Continuation-in-part of application No. 09/356,278, filed on Jul. 16, 1999, now abandoned.

(30) Foreign Application Priority Data

May 26, 1999 (CA) .............................................. 2272828

(51) Int. Cl.[7] .............................................. C08K 11/00
(52) U.S. Cl. ...................... 524/789; 524/445; 524/447; 524/790; 442/63
(58) Field of Search ............................... 524/445, 447, 524/789, 790; 442/63

(56) References Cited

U.S. PATENT DOCUMENTS

| | | | |
|---|---|---|---|
| 3,949,560 A | 4/1976 | Clem ............................... | 61/36 |
| 4,018,951 A | 4/1977 | Gross ............................. | 427/401 |
| 4,032,701 A | 6/1977 | Hughes ........................... | 526/88 |

(List continued on next page.)

FOREIGN PATENT DOCUMENTS

| | | | | |
|---|---|---|---|---|
| CA | 1310569 | 11/1992 | .............. | 154/70.03 |
| CN | 85102156 A | 1/1987 | | |
| DE | 3912765 A1 | 10/1990 | .............. | C09K/3/10 |
| DE | 195 31 002 A1 | 2/1997 | .............. | C09K/3/10 |
| EP | 0 290 814 | 11/1988 | .............. | C08F/20/06 |
| EP | 0 370 646 | 5/1990 | | |
| EP | 0 693 508 A1 | 1/1996 | .............. | C08F/220/56 |
| JP | 62-243606 | 10/1987 | .............. | C08F/2/44 |
| JP | 63-28639 A | * 2/1988 | | |
| JP | 63-028639 | 2/1988 | .............. | A41B/13/02 |
| WO | WO 94/05863 | 3/1994 | .............. | E02D/31/00 |
| WO | WO 99/14288 | 3/1999 | .............. | C09K/17/16 |

OTHER PUBLICATIONS

Blumstein, A. "Polymerization of Adsorbed Monolayers I. Preparation of the Clay–Polymer Complex" *Journal of Polymer Science: Part A* 3: 2653–2664; 1965.

Blumstein, R. et al. "Polymerization of Monomolecular Layers adsorbed on Montmorillonite: Cyclization in Polyacrylonitrile and Polymethacrylonitrile" *Applied Polymer Symposium* 25: 81–88; 1974.

Daniel, David E. "Geosynthetic Clay Liners, Part Two: Hydraulic Properties" *Geotechnical Fabrics Report* 14: 5:22–26; Jun./Jul. 1996.

(List continued on next page.)

*Primary Examiner*—Helen L. Pezzuto
(74) *Attorney, Agent, or Firm*—Kurt D. Van Tassel; Deborah G. VandenHoff; Van Tassel & Associates

(57) ABSTRACT

A reinforced networked polymer/clay alloy composite is produced by contacting a monomer/clay mixture with a reinforcing agent. The monomer/clay mixture comprises a monomer, a cross-linking agent and clay particles. An initiator means is used to initiate polymerization of the monomer/clay mixture, while the cross-linking agent concurrently acts to network oligomeric and polymeric species formed during polymerization to produce a networked polymer/clay alloy in the presence of the reinforcing agent. The networked polymer/clay alloy is intimately integrated with the reinforcing agent such that, on exposure to water, the networked polymer/clay alloy swells with substantially no clay separating from the composite.

57 Claims, 12 Drawing Sheets

U.S. PATENT DOCUMENTS

| | | | |
|---|---|---|---|
| 4,048,373 A | 9/1977 | Clem | 428/454 |
| 4,103,499 A | 8/1978 | Clem | 61/50 |
| 4,139,588 A | 2/1979 | Clem | 264/232 |
| 4,178,221 A | 12/1979 | Boutin et al. | 204/159.23 |
| 4,283,517 A | 8/1981 | Perricone et al. | 526/229 |
| 4,295,987 A | 10/1981 | Parks | 252/194 |
| 4,418,163 A | 11/1983 | Murakami et al. | 523/205 |
| 4,467,015 A | 8/1984 | Clem | 428/454 |
| 4,500,670 A | 2/1985 | McKinley et al. | 524/445 |
| 4,565,468 A | 1/1986 | Crawford | 405/270 |
| 4,731,067 A | 3/1988 | Le-Khac | 604/367 |
| 4,735,987 A | 4/1988 | Morita et al. | 524/436 |
| 4,738,867 A | 4/1988 | Itoh et al. | 427/44 |
| 4,810,573 A | 3/1989 | Harriet | 428/331 |
| 4,867,526 A | 9/1989 | Arroyo | 350/96.23 |
| 4,889,885 A | 12/1989 | Usuki et al. | 524/445 |
| 4,892,754 A | 1/1990 | Itoh et al. | 427/54.1 |
| 4,977,192 A | 12/1990 | Martineu et al. | 521/56 |
| 5,145,906 A | 9/1992 | Chambers et al. | 524/732 |
| 5,174,231 A | 12/1992 | White | 112/420 |
| 5,185,409 A | 2/1993 | Sortwell | 526/62 |
| 5,237,945 A | 8/1993 | White | 112/420 |
| 5,244,934 A | 9/1993 | Umeda et al. | 522/129 |
| 5,352,287 A | 10/1994 | Wason et al. | 106/416 |
| 5,413,747 A | 5/1995 | Akers et al. | 264/211 |
| 5,462,972 A | 10/1995 | Smith et al. | 521/53 |
| 5,489,469 A | 2/1996 | Kobayashi et al. | 428/283 |
| 5,578,219 A | 11/1996 | Kajita | 210/730 |
| 5,580,630 A | 12/1996 | Byrd | 428/47 |
| 5,584,609 A | 12/1996 | Clarey et al. | 405/270 |
| 5,614,269 A | 3/1997 | Hoskins et al. | 427/512 |
| 5,672,633 A | 9/1997 | Brehm et al. | 521/53 |
| 5,756,159 A | 5/1998 | Hoskins et al. | 427/394 |
| 5,760,121 A | 6/1998 | Beall et al. | 524/450 |
| 5,858,535 A | 1/1999 | Wang et al. | 428/407 |
| 5,877,248 A | 3/1999 | Beall et al. | 524/450 |
| 5,880,197 A | 3/1999 | Beall et al. | 524/445 |
| 5,980,996 A | 11/1999 | Terry et al. | 427/513 |

OTHER PUBLICATIONS

Kato, C. et al. "Preparation and Electrical Properties of Quaternary Ammonium Montmorillonite–Polystyrene Complexes" *Clay and Clay Minerals* 29: 4: 294–298; 1981.

Koerner, Robert M. *Designing with Geosynthetics* $3^{rd}$ ed., Prentice–Hall; pp. 624–644; 1994.

Nagae, H. et al. "Adsorption and Polymerisation of Acrylamide in Na–Montmorillonite and Na–Fluor–Tetrasilicic Mica" *Kobunshi Ronbun* 47: 8: 631–638; 1990, Abstract on p. 637.

Ogawa, M. et al. "Preparation of Montmorillonite–Polyacrylamide Interaction Compounds and the Water Absorbing Property" *Clay Science* 7: 243–241; 1989.

Pramanik, P. "Nano Composites of Clay and Polymer" *Popular Plastics & Packaging* 63–68; Jun. 1997.

Srikhirin, T. et al. "Polydiacetylene–Inorganic Clay Nanocomposites" *Polymers for Advanced Technologies* 9: 491–503; 1998.

Well, Larry W. "Building a Better Barrier" *ASTM Standardization News* 19–23; Jul. 1997.

\* cited by examiner

REINFORCED NETWORKED POLYMER/CLAY ALLOY COMPOSITE

This application is a continuation-in-part of U.S. patent application Ser. No. 09/356,278, filed in the name of Zhou et al on Jul. 16, 1999, now abandoned.

FIELD OF THE INVENTION

The present invention relates to absorbent materials. More specifically, the invention relates to a reinforced networked polymer/clay alloy composite useful, for example, in containment applications such as landfill liners or covers, reservoir liners, underground storage tank liners, secondary containment liners, and man-made bodies of water, or personal care absorbent articles, including diapers, training pants, feminine hygiene products such as sanitary napkins, incontinence devices and the like.

BACKGROUND DISCUSSION

There are a number of commercial applications for absorbent materials, including, without limitation, in containment applications as landfill liners or covers, reservoir liners, underground storage tank liners, secondary containment liners, and man-made bodies of water, or personal care absorbent articles, including diapers, training pants, feminine hygiene products such as sanitary napkins, incontinence devices and the like. While the applications are diverse, there is need for a material having improved water absorbency and/or fluid barrier properties.

For example, in waste containment applications, hydraulic barriers can reduce the escape or leakage of harmful leachates into surface and ground waters. In man-made bodies of water, a hydraulic barrier acts to contain the water within an enclosure or defined impoundment area.

In one type of liner, hydraulic barriers are often formed from bentonite. Specifically, bentonite is admixed with the soil forming the water-holding area. Upon contact of the bentonite with water, the bentonite swells and thereby fills up the voids found in the soil. However, the water absorption capacity of bentonite alone may not be sufficient for the containment of some water-soluble wastes.

U.S. Pat. No. 3,949,560 (Clem, Apr. 13, 1976) is directed to a soil sealant composition dry mixed with soil. The soil sealant composition consists of bentonite, a water-soluble dispersing agent and a pre-formed water-soluble polymer. The water-soluble dispersing agent is a phosphoric acid salt, sulfate of $ROSO_3X$ (R is a $C_8$–$C_{32}$ hydrocarbon, X is an alkaline metal or ammonium) or a leonardite salt. The pre-formed water-soluble polymer is polyacrylic acid, water-soluble salts of polyacrylic acid, hydrolyzed polyacrylonitrile, polyvinyl acetate, polyvinyl alcohol, copolymers of the foregoing or a copolymer of acrylic acid and maleic anhydride. A water containing enclosure is formed from the soil/soil sealant mixture and contacted with water to hydrate the bentonite. The resulting hydrated enclosure is used for containing water contaminated with industrial waste. No reinforcing agent is used with the soil/soil sealant mixture.

U.S. Pat. No. 4,048,373 (Clem, Sep. 13, 1977), U.S. Pat. No. 4,103,499 (Clem, Aug. 1, 1978) and U.S. Pat. No. 4,139,588 (Clem, Feb. 13, 1979) all describe a water barrier panel or moisture impervious panel comprised of a soil sealant sandwiched between two paperboard sheets. More particularly, the panel is formed of a corrugated paperboard carrier or form including a pair of spaced paperboard facing sheets interconnected by a paper corrugated strip to form a plurality of voids. The voids are filled with the soil sealant composition described in U.S. Pat. No. 3,949,560 and the edges of the panel may be sealed with wax, tape or water-soluble gum. When contacted with water, moisture passes through the paperboard sheets to the soil sealant composition, where the bentonite swells.

More recently, so-called geosynthetic clay liners ("GCL") have become relatively widely accepted for use as hydraulic barriers. A GCL has a layer of bentonite supported by a geotextile or a geomembrane material, mechanically held together by needling, stitching or chemical adhesives.

An example of a GCL prepared with a chemical adhesive is provided in U.S. Pat. No. 4,467,015 (Clem, Aug. 21, 1984). This patent describes a waterproofing structure or water impervious sheet material comprised of layers of flexible carrier sheets coated with a water swellable composition. The water swellable composition is clay or a dry granular mixture of clay, a pre-formed water-soluble polymer, such as polyacrylic acid, and a water-soluble salt. The composition is secured by using an adhesive, whether water-soluble or -insoluble or a solvent-soluble or -insoluble adhesive. A disadvantage of this type of laminate is that clays in the GCL may still migrate away from the GCL with the leachate percolating through the liner, albeit very slowly.

Similarly, U.S. Pat. No. 4,810,573 (Harriet, Mar. 7, 1989) describes a laminated composite article with a clay composition adhered to a water-impermeable sheet. The clay composition is an intimate mixture of water swellable clay and a pre-formed elastomer, such as polypropylene and/or polybutene. The intimate clay/elastomer mixture is produced by blending clay with pre-formed elastomers in a sigma blender to masticate the elastomer. The clay composition is adhered to the water-impermeable sheet by rolling to form a laminate. U.S. Pat. No. 5,580,630 (Byrd, Dec. 3, 1996) describes a multi-layer article using the same clay composition as Harriet.

As indicated above, rather than using a chemical adhesive, the layers of the GCL may be mechanically held together by other means such as stitching and needle punching. For instance, U.S. Pat. No. 4,565,468 (Crawford, Jan. 21, 1986) described a moisture impermeable barrier comprised of two fabric layers quilted together. A top sheet member is positioned over a base sheet member having a layer of bentonite resting on its upper surface. The top sheet member is secured to the base sheet member by stitches extending therebetween. The stitching forms either quilted compartments or elongated corrugated compartments containing the bentonite therein.

DE 3704503 A1 (Heerten et al.) discloses an article having two fabric layers sandwiching a bentonite clay layer, wherein the two fabric layers are needle punched together. U.S. Pat. No. 5,174,231 (White, Dec. 29, 1992) describes a multi-layer article including an intermediate layer of a water-swellable colloidal clay sandwiched between two layers of flexible material or fabric sheet. The two layers are structurally interconnected through the intermediate clay layer such as by needle punching, sewing, quilting, or needle looming, to interconnect fibers of one fabric layer to the other fabric layer at spaced locations over essentially the entire surface areas of both layers.

Thus, in these GCLs, the clay particles are either adhered onto the geotextile or geomembrane or are physically confined by opposing layers of geotextile or geomembrane. The opposing layers of geotextile or geomembranes are mechanically held together by means such as sewing, quilting and needle punching, which limits the movement of clay particles therebetween. However, the clay particles in granular bentonite used in these applications are typically a couple of micrometers or less in diameter. Further, the void spaces in the geotextiles or geomembranes and the spacing of the stitching or needle punching tend to be greater than the size of the clay articles. Thus, it is still possible for the clay particles in the GCL to migrate out of the liner, particularly when placed under a hydraulic pressure gradient, albeit slowly.

It is commonly known that bentonite swells well in fresh water but poorly in, water containing salts and/or metals, such as saltwater, seawater, acid mine drainage, and the like. Thus, while GCL's are effective barriers for fresh water, they are ineffective barriers to water with high salt and dissolved metals concentrations.

Another problem with GCL's is that the bentonite is typically dry and, therefore, until the bentonite swells, waste water can flow through the GCL. Accordingly, GCL's must first be pre-hydrated after installation. This pre-hydration step can take up to 48 hours, for example.

Yet another problem with GCL's is their weight. Typically, a GCL weighs more than 5 kg/M$^2$. Because of its weight, transportation and installation costs are significant.

Accordingly, there is a need for an absorbent material for containment applications, especially environmental containment applications, which is salt water and contaminant resistant. Also, there is a need for a barrier liner that is lighter than GCL, but having substantially comparable or improved barrier properties versus GCL. Moreover, there is a need for an absorbent material having intimately integrated components that do not disperse and/or migrate from the product, particularly when exposed to or immersed in water, and can effectively absorb water containing salt and/or metals.

SUMMARY OF THE INVENTION

According to the invention, there is provided a process for producing a reinforced networked polymer/clay alloy composite, comprising the steps of: (a) preparing a monomer/clay mixture by mixing at least a monomer, clay particles, a cross-linking agent, and a mixing fluid in a vessel; (b) contacting the monomer/clay mixture and a reinforcing agent; (c) exposing the monomer/clay mixture to a polymerization initiator means; and (d) polymerizing the monomer/clay mixture in the presence of the reinforcing agent so that a reinforced networked polymer/clay alloy composite is formed.

According to the invention, there is also provided a product produced by the process described above.

According to the invention, there is further provided a reinforced networked polymer/clay alloy composite comprising a networked polymer/clay alloy, wherein the alloy is a chemically integrated composition of polymer and clay, and the alloy is intimately integrated with a reinforcing agent so that, when the composite is immersed in deionized water, at a temperature in a range of from about 20° C. to about 30° C., the alloy swells with substantially no clay separating from the composite.

According to the invention, there is provided the method of using the reinforced networked polymer/clay alloy composite as an absorbent material for a personal care product or as a fluid barrier in a confining stress range of from about 0 kPa to about 10000 kPa, wherein, when placed under a zero confining stress, the barrier has a deionized water flux less than about $1 \times 10^{-8}$ m$^3$/m$^2$/s.

BRIEF DESCRIPTION OF THE DRAWINGS

The reinforced networked polymer/clay alloy composite and the process for producing the reinforced networked polymer/clay alloy composite of the present invention will be better understood by referring to the following detailed description of preferred embodiments and the drawings referenced therein, in which.

DETAILED DESCRIPTION OF PREFERRED EMBODIMENTS

Definitions

Figure 1:
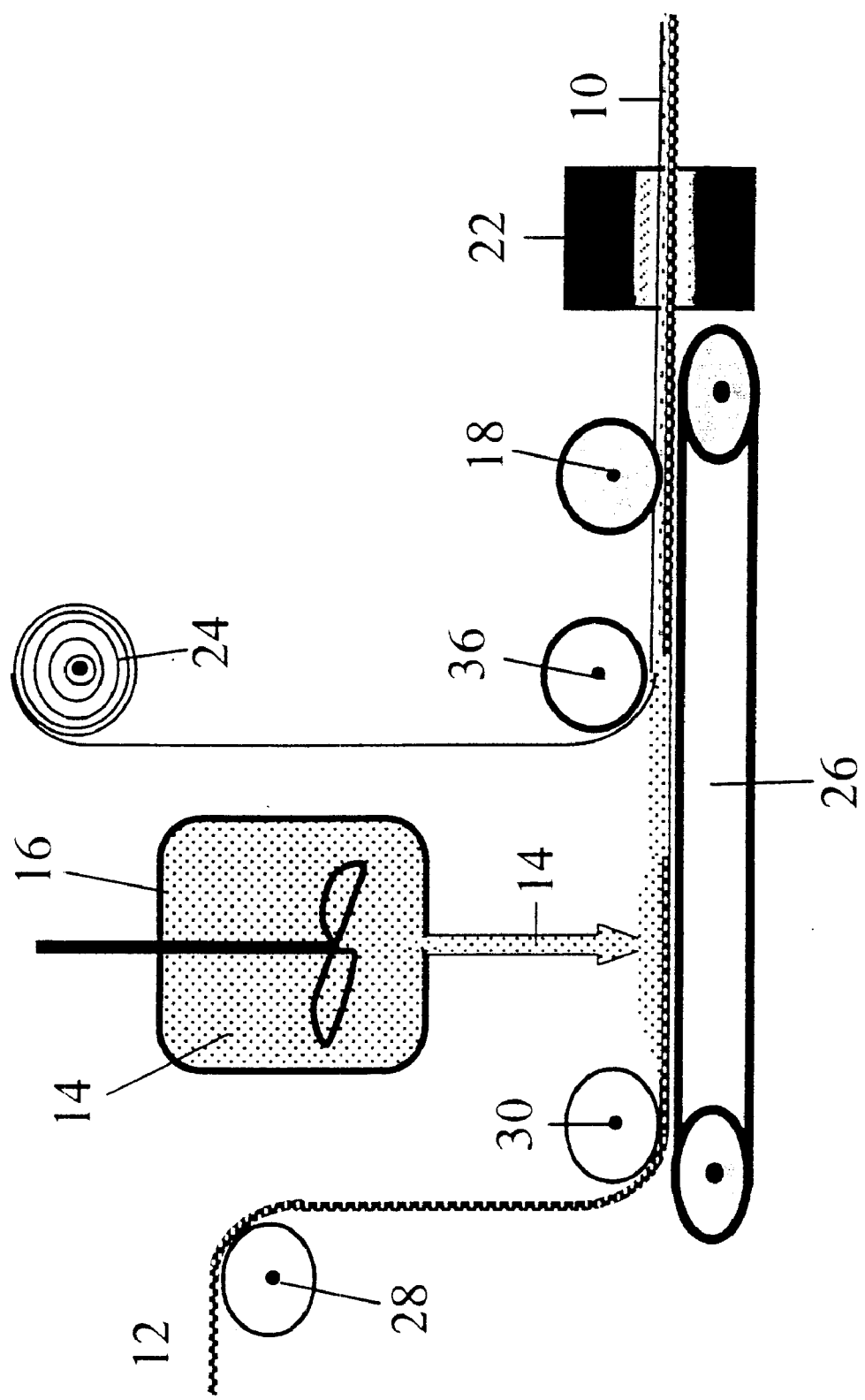
FIG. 1 is a schematic of one embodiment of an apparatus for use in producing one embodiment of the reinforced networked polymer/clay alloy composite.

"Monomer" is an organic molecule that can combine with a number of the same or different molecules to form a large molecule having repeating monomeric units, wherein the repeating monomeric units have a similar chemical architecture and atom composition as the monomeric units.

"Polymer" is a large molecule built from the same or different repeating monomeric units and typically has a molecular weight in a range from about 10,000 to about 20,000,000. Polymer, as used herein, also includes any polymer made from two or more different repeating units, such as copolymers (i.e., comprising two different monomeric units), terpolymers (i.e., comprising three different monomeric units), tetrapolymers (i.e., comprising four different monomeric units) and so on. Moreover, the repeating monomeric units can alternate in a sequential pattern (e.g., A—B—A—B), block pattern (e.g., A—A—B—B), random pattern (A—B—B—A—B—A) or combinations thereof.

"Oligomer" is also built from the same or different repeating monomer units but is a smaller molecule than a polymer and typically has a molecular weight in a range of from about 200 up to about 9,000.

"Polymerization Initiator Means" is a chemical substance, gamma ray irradiation, X-ray irradiation, irradiation by high energy sub-atomic particles, each type of radiation having a wavelength less than about 10 nm, (collectively, high energy irradiation) and combinations thereof that can increase the reactivity of a monomer so that a polymerization or oligomerization chain reaction between monomers is initiated and a polymer or oligomer is formed. At the appropriate temperature, certain chemical substances become either an ionic or free radical species that can react with a monomer alone to produce an ionic or free radical monomeric species, which can, in turn, react with another monomer, thereby initiating a polymerization reaction. Also, high energy irradiation can be used to produce an ionic or free radical monomeric species from a monomer and/or a chemical substance other than a monomer to initiate a polymerization reaction.

"Cross-linking Agent" is a chemical substance, photons produced from a radiation source and combinations thereof that assist in forming a bridging moiety between two or more backbone structures formed by multiple monomeric units (e.g., oligomeric or polymeric units). Thus, a cross-linking agent can bridge oligomeric or polymeric species either during or after their formation.

"Networked Polymer" is a very large polymer molecule formed by cross-linking multiple oligomers and/or polymers to form an interconnected polymeric network. A networked polymer can have cross-linking moieties between oligomers and/or polymers, where the moieties are formed from either the cross-linking agent itself, branches attached to the backbone of each oligomer and/or polymer or combinations thereof.

"Networked Polymer/Clay Alloy" ("NPC Alloy") is a chemically integrated composition of polymer and clay. Clay particles form a unique chemical association with the networked polymer as it is formed. The chemical association may be, for example, without limitation, through hydrogen bonding, ionic bonding, Van der Waal's/dipole bonding, affinity bonding, covalent bonding and combinations thereof.

"Reinforcing Agent" is a material having a sufficiently porous or permeable structure so that a networked polymer, and/or an NPC alloy can form around and/or in the material's structure, thereby providing additional support and/or strength to the aforementioned networked polymer or polymer/clay compositions.

"Reinforced Networked Polymer/Clay Alloy Composite" ("Reinforced NPC Alloy Composite") is a macroscopic combination comprising a reinforcing agent and an NPC alloy. There is an intimate three-dimensional integrated association between composite components, as opposed to a simple two-dimensional laminate composite, where there is no integration along a third dimension.

General Discussion

A reinforced NPC alloy composite of the present invention is an absorbent material useful, for example, without limitation, in containment applications such as landfill liners or covers, reservoir liners, underground storage tank liners, secondary containment liners, and liners for man-made bodies of water, or personal care absorbent articles, including diapers, training pants, feminine hygiene products such as sanitary napkins, incontinence devices and the like.

In containment applications, the composite material preferably absorbs water to form a barrier, which then has a relatively low permeability to water, oil and other liquids. In personal care articles, the composite material preferably has a high water absorbency capacity. As discussed more fully below, the properties of the reinforced NPC alloy composite can be adjusted depending on the application.

The reinforced NPC alloy composite of the present invention has improved resistance to chemical, electromagnetic radiation and biological degradation in surface and subsurface conditions. By improved resistance to chemical degradation, we mean that the composite has improved resistance to, for example, without limitation, salt water and drainage fluids with high heavy metal content and/or acidic pH. By improved resistance to electromagnetic degradation, we mean that the composite has an improved resistance to ultraviolet (UV) and other potentially detrimental electromagnetic radiation. By improved resistance to biological degradation, we mean that the NPC alloy would be more resistant to bacterial attack after installation, as compared with a polymer without clay.

For example, the permeability of a liner produced with the reinforced NPC alloy composite is not significantly affected by salt water, or other aqueous solutions with heavy metals and/or acidic pH. Thus, the composite represents an improvement over a conventional GCL liner, which typically loses its effectiveness on exposure to salt water.

As another example, polyacrylamide is stable at surface and sub-surface conditions. However, it is susceptible to chemical and UV degradation. The clay reduces degradation in the NPC alloy by protecting the polymer. Also, the NPC alloy is more resistant to biological degradation than, for example, polyacrylic acid alone.

When used in barrier applications, the reinforced NPC alloy composite weighs less than a conventional GCL per unit area. Also, the reinforced NPC alloy composite can be used without pre-hydration, as is often required for conventional GCL's.

A reinforced NPC alloy composite is produced by intimately distributing a mixture of monomer, clay particles, a cross-linking agent and a mixing fluid (i.e., an MCX mixture) in, on and/or among a reinforcing agent, such as a porous substrate or non-aggregated fibers. By "intimately distributing", "intimate distribution" or "intimately distributed", we mean that an MCX mixture is distributed throughout the porous substrate or non-aggregated fibers so that a substantial portion of the surfaces, voids and interstitial spaces of and/or between the fibers or substrate is covered and/or occupied with the MCX mixture. Preferably, the MCX mixture is intimately distributed substantially through the thickness of the reinforcing agent.

After the MCX mixture is intimately distributed in, on and/or among the reinforcing agent, the MCX mixture is polymerized. The clay particles are chemically associated with the networked polymer as it is formed to produce an NPC alloy. Because of the intimate MCX mixture distribution, the NPC alloy is intimately integrated with the reinforcing agent.

The polymer and clay in the NPC alloy cooperate physically and chemically (i.e., physicochemically) to contribute to the reinforced NPC alloy composite's water absorbency.

Thus, the composite can swell substantially as an integrated unit while only negligible amounts of clay, if any, (i.e., substantially no clay) separate from the composite when it is immersed in deionized water at temperatures in a range of from about 1° C. to about 60° C.

Monomer/Clay Mixture

The monomer/clay mixture used in making the NPC alloy includes, without limitation, a monomer, clay particles, a cross-linking agent and a mixing fluid. For brevity, we may refer to the mixture of monomer, clay, cross-linking agent and mixing fluid as "MCX."

The monomer is at least partially soluble in the mixing fluid. A monomer soluble in the mixing fluid may be mixed with other monomers that are soluble or insoluble in the mixing fluid. Preferably, at least one water-soluble monomer has the following general formula:

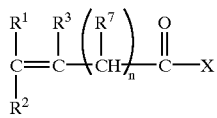

wherein X is selected from the group consisting of OM, $OR^4$ and $NR^5R^6$, M is an alkali or alkaline earth metal ion or $NH_4^+$, $R^1$, $R^2$, $R^3$, $R^5$, $R^6$ and $R^7$ are independently selected from the group consisting of H, $CH_3$, $CH_2CH_3$, $CH_2CH_2CH_3$, $CH(CH_3)_2$, $CH_2CH_2CH_2CH_3$, and CN, and $OR^4$ is selected from the group consisting of OH, $OCH_3$, $OCH_2CH_3$, $OCH_2CH_2CH_3$, $OCH(CH_3)_2$, $OCH_2CH_2CH_2CH_3$, $OCH_2CH_2OH$ and $(OCH_2CH_2)_mOH$, n=0 to about 10 and m=1 to about 10.

More preferably, the monomer is selected from the group consisting of acrylic acid (where $R^1$=H, $R^2$=H, $R^3$=H, n=0, X=$OR^4$, $R^4$=H), acrylamide (where $R^1$=H, $R^2$=H, $R^3$–H, n=0, X=$NR^5R^6$, $R^5$=H, $R^6$=H), sodium acrylate (where $R^1$=H, $R^2$=H, $R^3$=H, n=0, X=OM, M=Na), potassium acrylate (where $R^1$=H, $R^2$=H, $R^3$=H, n=O, X=OM, M=K), methacrylic acid (where $R^1$=H, $R^2$=H, $R^3$=$CH_3$, n=0, X=$OR^4$, $R^4$=H), N-isopropylacrylamide (where $R^1$=H, $R^2$=H, $R^3$=H, n=0, X=$NR^5R^6$, $R^5$=$CH(CH_3)_2$, $R^6$=H), and combinations thereof.

An example of a monomer that can be co-polymerized with a monomer of the above general formula are vinyl esters, such as vinyl acetate. Vinyl acetate is readily co-polymerized and may be retained as a vinyl acetate moiety or subsequently hydrolyzed to the corresponding vinyl alcohol.

The clay particles may be swelling or non-swelling clays. Suitable swelling clay particles include, without limitation, montmorillonite, saponite, nontronite, laponite, beidellite, iron-saponite, hectorite, sauconite, stevensite, vermiculite, and combinations thereof. Suitable non-swelling clay particles include, without limitation, kaolin minerals (including kaolinite, dickite and nacrite), serpentine minerals, mica minerals (including illite), chlorite minerals, sepiolite, palygorskite, bauxite, silica and combinations thereof.

Preferably, the clay is a swelling clay such as, for example, smectite and vermiculite type clays. More preferably, the clay is a smectite type clay. Examples of suitable smectites are, without limitation, montmorillonite (sometimes referred to as bentonite), beidellite, nontronite, hectorite, saponite, sauconite and laponite. Bentonite is an example of a naturally-occurring combination of clay particles. Bentonite is a rock rich in montmorillonite and may also comprise other smectites as well as other non-clay mineral constituents. Consequently, montmorillonites or their mixtures with other smectites are often referred to simply as bentonite. Bentonite clays are fine crystals or particles, usually plate-like in shape, with a lateral dimension up to 2 μm and a thickness in a range of a few to tens of nanometers (nm).

Swelling clays have the ability to absorb water and are less expensive than monomer. Accordingly, the reinforced networked polymer composite of the present invention is less expensive than one produced without clay. Moreover, clay particles are resistant to degradation in long-term environmental applications, while still providing water absorbency for long periods of time.

Non-swelling clays would provide increased resistance to salt water for the reinforced NPC alloy composite. Also, non-swelling clays, like swelling clays, are less expensive than monomer and would reduce the composite's cost.

Preferably, the weight ratio of clay to monomer in the MCX mixture is in a range of from about 0.05:1 to about 19:1. More preferably, the weight ratio of clay to monomer in the MCX mixture is in a range of from about 0.5:1 to about 3:1.

Suitable chemical substances for use as cross-linking agents include, without limitation, N,N'-methylene bisacrylamide, phenol formaldehyde, terephthalaldehyde, allylmethacrylate, diethyleneglycol diacrylate, ethoxylated trimethylolpropane triacrylate, ethylene carbonate, ethylene glycol diglycidal ether, tetraallyloxyethane, triallylamine, trimethylolpropanetriacrylate, and combinations thereof.

As a general rule, depending on the selected polymerization reaction time and temperature, a higher ratio of cross-linking agent to monomer will generally produce a lower concentration of residual monomer, but the networked polymer's water absorption capacity (WAC) may drop if the ratio gets too high. The weight ratio of the cross-linking agent to the monomer is preferably in a range of from about 0.05:100 to about 1.5:100. More preferably, the weight ratio of the cross-linking agent to the monomer is in a range of from about 0.05:100 to about 0.7:100. Most preferably, the weight ratio of the cross-linking agent to the monomer is in a range of from about 0.1:100 to about 0.5:100.

The mixing fluid is a polar solvent. Examples of suitable mixing fluids include, without limitation, water, alcohol, oxygen-containing organic solvents, and combinations thereof, in which the monomer can be at least partially dissolved. Examples of suitable oxygen-containing organic solvents include, without limitation, alcohols, glycols, polyols, sulfoxides, sulfones, ketones and combinations thereof. Preferably, the mixing fluid is water, alcohol or a combination thereof. Most preferably, the mixing fluid is water.

Preferably, the amount of mixing fluid in the MCX mixture is in a range of from about 30% to about 90% by weight. More preferably, the amount of mixing fluid in the MCX mixture is in a range of from about 40% to about 80% by weight. Most preferably, the amount of mixing fluid in the MCX mixture is in a range of from about 40% to about 60% by weight.

Additionally, the MCX mixture preferably comprises one or more additives. Buffering agents and/or neutralizing agents may be used as additives to maintain the pH of the mixture in a predetermined range and/or neutralize acidic and/or basic monomers.

Also, metal complexing agents may be used as additives to form metal complexes, thereby sequestering metal ions that might otherwise interfere with forming the NPC alloy. For example, acrylamide monomer is typically manufactured with cupric salts as a stabilizer (e.g., to inhibit polymerization during shipment or in storage). Thus, a metal complexing agent, such as a sodium carbonate or ethylenediaminetetracetic acid (EDTA), can be added to the MCX mixture to complex the metal ion and thereby sequester the metal. It should be understood that some additives can be used to satisfy multiple functions. For example, sodium carbonate ($Na_2CO_3$) and sodium bicarbonate ($NaHCO_3$), could function as both a buffering agent (i.e., maintaining pH) and a neutralizing agent (i.e., neutralizing acidic monomers), while also working as a metal complexing agent. Therefore, it will be apparent to those skilled in the art that one or more additives can be used for forming an NPC alloy depending on the monomer and cross-linking agent used, type of stabilizing agent mixed with the monomer, type of polymerization reaction and the desired reaction pH and temperature.

Examples of buffering agents and/or neutralizing agents include, without limitation, sodium hydroxide, potassium hydroxide, ammonium hydroxide, sodium carbonate, sodium bicarbonate, potassium carbonate, potassium bicarbonate, oxylate-containing compounds, sulfate-containing compounds, phosphate-containing compounds, and combinations thereof.

Examples of metal complexing agents include, without limitation, sodium carbonate, sodium bicarbonate, potassium carbonate, potassium bicarbonate, ethylenediaminetetraacetic acid (EDTA), EDTA salts, orthophosphate, pyrophosphate, metaphosphate, hydrogen phosphate, and combinations thereof.

Each of the components of the MCX mixture may be added in any order. Preferably, however, the mixing fluid and monomer are mixed with any other desired component, followed by adding a chemical initiator and then adding the clay. Also, caution should be exercised in mixing any mixture components to avoid any significant exotherms. Otherwise, any significant exotherm should be allowed to cool. A large exotherm from mixing components might otherwise lead to premature polymerization shortly after the initiator is added, but before the mixture is intimately distributed in, on and/or among the reinforcing agent and heated under a controlled condition.

The MCX mixture forms a slurry type mixture, which should be mixed until it is substantially homogeneous.

Reinforcing Agent

The reinforcing agent may comprise non-aggregated fibers or a substrate having a porous structure. Examples of porous substrates include knitted, woven and non-woven, natural and synthetic fibers. Suitable synthetic fibers for either type of reinforcing agent include, for example, without limitation, polypropylene, polyester, polyamide, polyethylene fibers, and combinations thereof. Examples of suitable natural fibers include, without limitation, wood pulp, cotton, hemp, flax and asbestos fibers, and combinations thereof.

Preferred porous substrates for landfill applications include geotextile materials. Examples of suitable non-woven geotextiles are, without limitation, PETROMAT™ 4597 (Amoco), AMOCO 4551™, AMOCO 4553™, AMOCO 4506™, GEOTEX® (Synthetic Industries, Inc., Chattanooga, Tenn., U.S.A.) and TERRAFIX® 270R-A (Terrafix Geosynthetics Inc., Toronto, Ontario, Canada). Preferred geotextiles have a unit weight in a range of from about 0.1 to 0.8 kg/$m^2$.

Another preferred porous substrate is a geotextile bonded to a geomembrane. Presently, one type of geotextile-geomembrane laminate is commercially available from Vernon Plastics, Haverhill, Mass., USA.

Alternatively, the geotextile-geomembrane laminate could be formed in a continuous process by bonding a geomembrane material to a geotextile. For example, without limitation, suitable geomembrane materials are high density polyethylene (HDPE), polyvinyl chloride (PVC), very flexible polyethylene (VFPE), flexible polypropylene (fPP), chlorosulfonated polyethylene (CSPE), and combinations thereof. The geomembrane may be bonded to the geotextile, for example, without limitation, by heat, adhesive, and combinations thereof.

The geomembrane material can be applied to the porous substrate material either before or after the substrate material is mixed with the polymer/clay alloy mixture to form the NPC alloy composite. Preferably, however, the polymer/clay alloy mixture is dispersed in the substrate material using a roller or piston.

The use of a geotextile-geomembrane laminate as a reinforcing agent is particularly advantageous in some applications, for example land-fill applications, where it is desired to use both a primary liner (often a geomembrane) and a secondary liner (for example, a GCL). By using a geotextile-geomembrane laminate as a reinforcing agent, a reinforced NPC alloy composite can be installed in one step.

In certain applications, for example, as landfill liners and covers, it may be desirable to use a reinforcing agent that is resistant to biodegradation. In other applications, for example, personal care absorbent articles, it may be desirable to use a reinforcing agent that will biodegrade within a selected time period.

Whether the reinforcing agent is a porous substrate or non-aggregated fibers, the inventive process produces a non-laminated, but intimately integrated, composite between the reinforcing agent and the NPC alloy. Preferably, the reinforcing agent is dispersed homogeneously throughout the NPC alloy. However, a portion of NPC alloy may be formed that is substantially free of reinforcing agent (i.e., non-reinforced NPC alloy). Typically, a contiguous portion of non-reinforced NPC alloy is integrally connected with the reinforced NPC alloy and is formed on one side of the composite, usually its topside. To the extent the composite is made with a contiguous portion of non-reinforced NPC alloy layer, the non-reinforced contiguous portion is preferably less than about 2.5 mm deep. More preferably, the non-reinforced contiguous portion is less than about 1 mm deep and most preferably, it is less than 0.5 mm deep.

Also, the portions of non-reinforced NPC alloy formed may also be non-contiguous. In that case, however, the percentage of non-contiguous non-reinforced portions should be limited so that the overall structural integrity needed for composite's specific application is not compromised.

When the reinforcing agent comprises a substrate having a porous structure, the MCX mixture is added to the porous substrate so that an intimate distribution of the mixture in and/or on the substrate is achieved. When the MCX mixture is polymerized, a layer of NPC alloy may be formed on top of the substrate. But, because the MCX mixture is intimately distributed in and/or on the substrate, the layer on top of the substrate is also an integral part of the NPC alloy in the substrate and, therefore, an integral part of the composite.

When the reinforcing agent comprises non-aggregated fibers, the reinforcing agent is mixed into the MCX mixture. The MCX/fiber mixture is then distributed into a mold prior to polymerization. Alternatively, non-aggregated fibers may be distributed in a mold and the MCX mixture is poured over the fibers. The mold may be such so as to produce a sheet-like material or another suitable shape for other applications. The MCX/fiber mixture may be distributed in a mold, for example, without limitation, vibration, hydraulic loading, pressure, and combinations thereof.

The MCX mixture may be intimately distributed in and on the porous substrate by, for example, without limitation, vibration, rolling, scrubbing, spraying, hydraulic loading, pressure, vacuum and combinations thereof.

It will be understood that if a pre-formed geosynthetic dual liner is used or if the geomembrane is fused prior to polymerization, that intimate distribution means, other than a vacuum, will be used to intimately distribute the MCX mixture in and on the porous substrate.

Polymerization

After the MCX mixture is intimately distributed in, on and/or among the reinforcing agent, the polymerization process begins while the cross-linking agent, acting in concert with the polymerization process, helps to form a networked polymer/clay alloy structure that is intimately integrated with the reinforcing agent. Polymerization of the MCX mixture is initiated by a polymerization initiator means for generating an ionic or free radical monomeric species. Initiation may be accomplished by adding a suitable chemical substance to the MCX mixture. Also, electromagnetic radiation having a wavelength of 10 nanometers (nm) or less may be used alone or in combination with a chemical initiator.

Suitable chemical substances for initiating polymerization include, without limitation, free radical initiators, carbanions, carbonium ions, and combinations thereof.

Examples of free radical initiators include, without limitation, thermal initiators, and redox systems, which are typically two or more chemicals, which are added simultaneously as different solutions.

Examples of thermal initiators include, without limitation, (1) alkali metal salts of sulfite, bisulfite, persulfate, benzoyl peroxide, and combinations thereof, (2) ammonium salts of sulfite, bisulfite, persulfate, benzoyl peroxide, and combinations thereof, (3) 2,2'-azobis(2-amidino-propane)-dihydrochloride, (4) 2,2'-azobis(4-cyanopentanoic acid), and combinations thereof.

The desired polymerization temperature for forming an NPC alloy composite is primarily dependent on the type and concentration of initiator means selected. For example, lower polymerization temperatures may be used where a thermal initiator prone to forming free radicals at a lower temperature (e.g., about 40° C. to about 50° C.) is used. Thus, where the polymerization reaction used for making the NPC alloy is initiated with a thermal initiator, the reaction is preferably at a temperature in a range of from about 40° C. to about 95° C. More preferably, however, the reaction temperature is at a temperature in a range of from about 60° C. to about 85° C. and most preferably, in a range of from about 65° C. to about 80° C. Also, where a high energy radiation source, such as gamma ray radiation is used, the polymerization reaction may be conducted as low as about ambient temperature, for example about 20° C.

The polymerization reaction time is also primarily dependent on the type of initiator means used and its concentration. However, other factors affecting the desired reaction time include the type of monomer and its concentration, the depth of the MCX mixture and the amount of reinforcing agent (e.g., MCX mixture thickness as applied on the substrate or volume of non-aggregated fibers in the MCX mixture). Also, once a polymerization reaction is initiated, typically, it will not terminate in response to a sharp temperature drop. For example, once the MCX mixture is exposed to the desired initiation temperature, the polymerization reaction will proceed for some time thereafter, depending on the reaction temperature selected, the time period that the MCX mixture is exposed to the selected temperature (i.e., heat exposure period) and the composite's heat retention. Also, we have discovered that higher initiator concentrations generally produce residual monomer concentrations of about 200 ppm or less. However, these higher initiator concentrations are more likely to promote premature polymerization unless the temperature is kept sufficiently below 40° C. Accordingly, it is important to maintain the MCX mixture below 40° C. before the mixture is distributed in, on and/or among the reinforcing agent so that the mixture's viscosity is sufficiently low to ensure the mixture is intimately distributed in, on and/or among the reinforcing agent.

The time period that the MCX mixture is exposed to the selected reaction temperature may be in a range from as low as about 1 minute to as high as about 24 hours. For example, where an MCX mixture having a clay to monomer ratio of about 2:1 is pressed into a porous substrate to a depth of about 2–3 mm, potassium persulfate is used as a thermal initiator and the selected temperature is about 80° C., the duration of the heat exposure period is preferably in a range of from about 2 minutes to about 60 minutes. More preferably, under similar conditions, the heat exposure period is in a range of from about 2 minutes to 45 minutes and, most preferably, in a range from about 3 minutes to about 30 minutes.

Examples of redox systems include, without limitation, persulfate/bisulfite, persulfate/thiosulfate, persulfate/ascorbate, hydrogen peroxide/ascorbate couples, and combinations thereof. Typically, additional heat is not required when using a redox systems initiator because the reactions are often exothermic, so such systems can work effectively at temperatures in a range of from about the freezing point of the MCX mixture to the boiling point of the mixing fluid. Typically, the temperature is ambient, about 20° C.

Alternatively, polymerization may be initiated by electromagnetic radiation having a wavelength below about 10 nm such as, for example, without limitation, by gamma rays, X-rays, or high energy sub-atomic particles. In such a case, the polymerization reaction is typically conducted at ambient temperatures. However, the temperature can be higher or lower.

However, it is well known to those skilled in the art that UV radiation, with wavelengths ranging from about 200 nm to 390 nm is not suitable for polymerization initiation of the MCX mixture because the clay will interfere with UV light's ability to penetrate into the sample, and thereby initiate the polymerization reaction, even with a photo-initiator present. More specifically, it is believed that the clay preferentially absorbs the UV light, thereby inhibiting the UV light's effectiveness as an initiator means.

Optionally, once polymerized, all or a portion of the mixing fluid remaining in the reinforced NPC alloy composite product may be removed, for example by desiccating at room temperature or oven-drying. If oven-dried, the composite should be dried at a temperature that does not adversely affect the properties or characteristics of the product, for example, at a temperature less than about 110° C.

The moisture content of the reinforced NPC alloy composite product is dependent on the application and other factors. For example, a higher moisture content composite provides greater flexibility and a lower initial permeability. But a lower moisture content composite can have reduced transportation costs. Consequently, the desired moisture content will be determined by the environment in which the composite product will be used and maximum acceptable transportation costs.

Therefore, for a composite product with at least some flexibility, the moisture content is preferably in a range of from about 25% to about 75% by weight.

Reinforced NPC Alloy Composite

In use, the NPC alloy swells on contact with water as the alloy absorbs water. The expanded NPC alloy swells in and/or around the reinforcing agent. It is believed that the alloy swells and expands into any interstitial spaces that were not occupied by the NPC alloy when the composite was formed. Also, it is believed that the alloy expands around the reinforcing agent itself. Consequently, the composite swells substantially as an integrated unit while only negligible amounts of clay, if any (i.e., substantially no clay), separate from the composite when it is immersed in water at a temperature in a range of from about 1° C. to about 60° C., whether the water is saline or not.

It will be understood by those skilled in the art that the degree to which the NPC alloy is networked will affect the alloy's capacity to absorb water. Of course, if insufficient cross-linking agent is used, the NPC alloy may become water soluble under certain conditions and the clay could then substantially separate from the alloy. On the other hand, if excessive amounts of cross-linking agent are used, the NPC alloy may be so inflexible that it is unable to absorb sufficient amounts water and thereby reach either the desired fluid permeability and/or water absorption performance.

In containment applications, the reinforced NPC alloy composite product is often under a confining stress due to overburden. Under a standard effective confining stress of 20 kPa or 2.9 psi, the flux (i.e., the rate water travels at the specified pressure) of the composite is about $10^{-8}$ $m^3/m^2/s$ or less, as measured by ASTM 5887-95. As the confining stress increases with additional overburden, the hydraulic conductivity of the composite will decrease because the composite will become compressed.

Cover Sheet

A cover sheet is advantageously used to (1) assist in MCX mixture distribution, for example, when using a vacuum, (2) reduce evaporation and/or boiling of mixing fluid or other components in the MCX mixture during polymerization, and/or (3) assist in handling, for example rolling, and storage of the composite.

In one embodiment, a cover sheet can be contacted with the MCX mixture either during or shortly after the mixture is contacted with the reinforcing agent. Moreover, the cover sheet may be applied to one or both sides of the reinforcing agent contacted with the MCX mixture. But preferably, the cover sheet is applied to one side, and more preferably, the cover sheet is applied to the side opposing the side on which the means for distributing the MCX mixture (e.g., vacuum, roller, pressure, etc.) is applied. Most preferably, the cover sheet is concurrently contacted with the MCX mixture and reinforcing agent, while a vacuum is applied to the opposing side and thus the mixture is intimately distributed in, on and/or among the reinforcing agent.

In another embodiment, the cover sheet may be applied to one or both side of the reinforced NPC alloy composite after polymerization. If desired, the cover sheet may be self-adhering to the composite or may be adhered to the composite, for example, without limitation, by heat bonding or an adhesive.

Examples of suitable cover sheets include, without limitation, polyethylene film, sulfite and sulfate papers, kraft papers, groundwood papers, filter papers, woven and non-woven natural and synthetic fabrics, fiberglass, and combinations thereof. The cover sheet may be removed after polymerization or left in place, depending on the composite's ultimate application.

Illustrative Process

Figure 2:
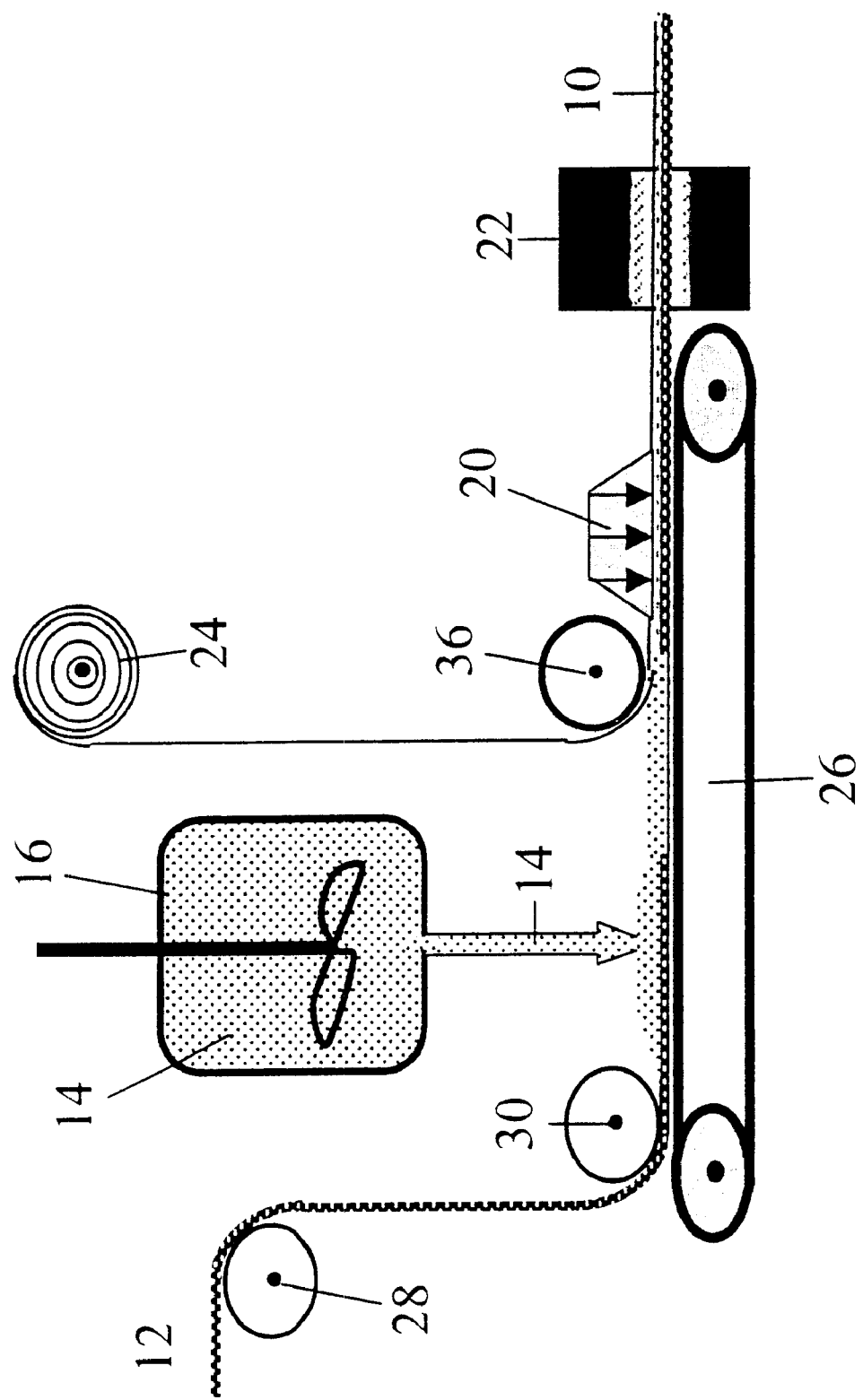
FIG. 2 is a schematic of another embodiment of an apparatus for use in producing one embodiment of the reinforced networked polymer/clay alloy composite.
Figure 3:
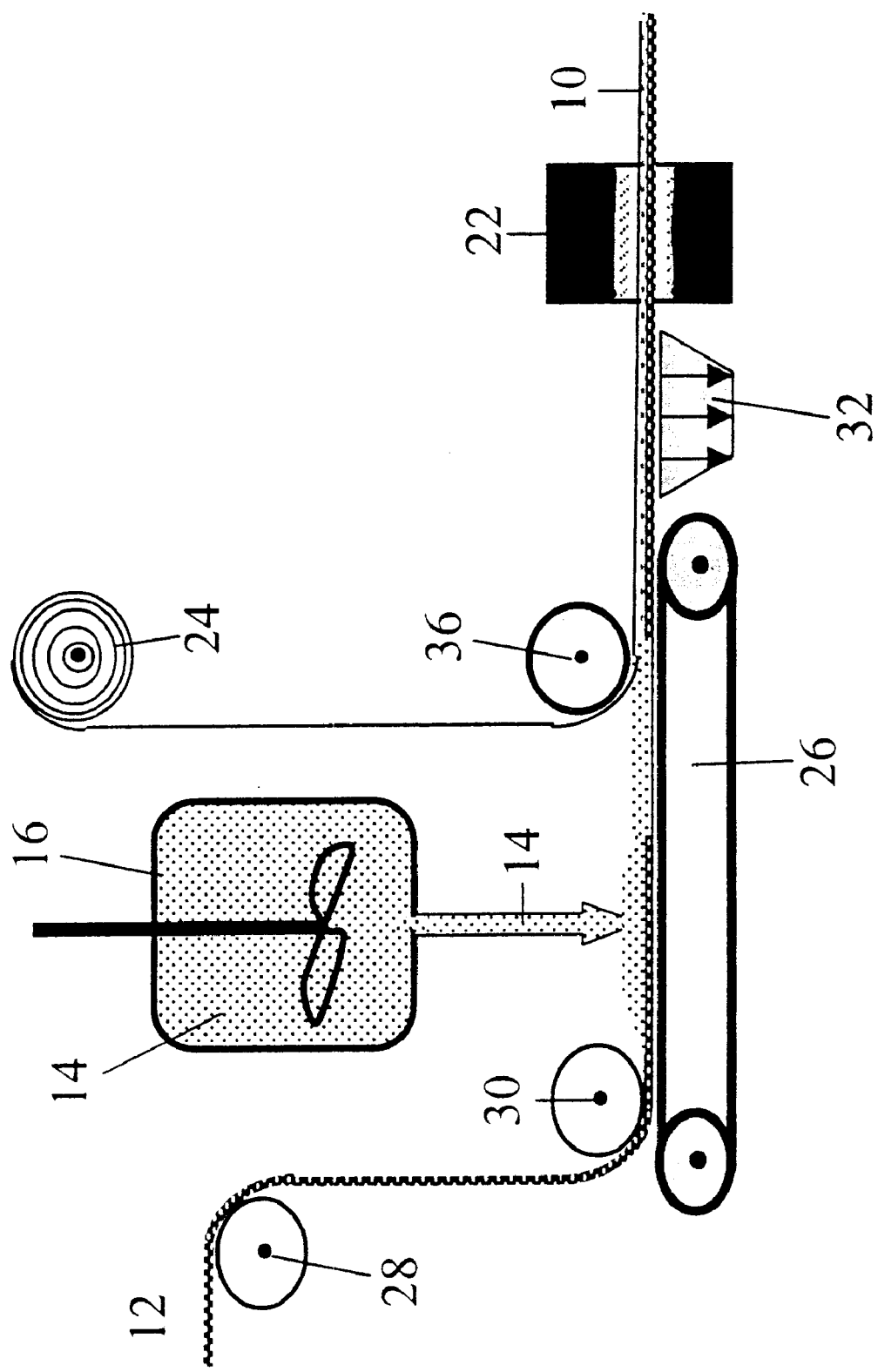
FIG. 3 is a schematic of a further embodiment of an apparatus for use in producing one embodiment of the reinforced networked polymer/clay alloy composite.

FIGS. 1–3 illustrate a process for producing a reinforced NPC alloy composite 10. A reinforcing agent, in this case a porous substrate 12, is fed onto a conveyor 26, using feeder rollers 28, 30.

An MCX mixture 14 is prepared in vessel 16, by mixing at least a monomer, clay particles, a cross-linking agent and a mixing fluid until the mixture is substantially homogeneous. Preferably, the MCX mixture 14 is maintained in the vessel 16 at a temperature less than about 40° C., to reduce premature polymerization of the monomer.

The MCX mixture 14 is metered from the vessel 16 and contacts the porous substrate 12 as it moves along the conveyor 26. A cover sheet 24 is placed on top of the MCX mixture 14 using a guiding roller 36.

In the embodiment illustrated in FIG. 1, the porous substrate 12 is contacted with the MCX mixture 14, using a roller 18, until the mixture 14 is distributed in and on the substrate 12.

In the embodiment illustrated in FIG. 2, the porous substrate 12 is contacted with the MCX mixture 14, using a piston 20, until the mixture 14 is intimately distributed in and on the substrate 12. Piston 20 may be a mechanical or gas piston.

In the embodiment illustrated in FIG. 3, the porous substrate 12 is contacted with the MCX mixture 14, using a vacuum means 32, until the mixture 14 is intimately distributed in and on the substrate 12.

In all the illustrated embodiments, after the MCX mixture 14 is intimately distributed in and/or on the porous substrate 12, the mixture 14 is, in accordance with the above discussion, polymerized within and on the substrate 12 by heating the combined substrate 12 and mixture 14 in a heating zone 22 to form the reinforced NPC alloy composite 10. The reinforced NPC alloy composite 10 can be rolled and packaged for subsequent handling and transport, if desired.

The following non-limiting examples of embodiments of the present invention that may be made and used as claimed herein are provided for illustrative purposes only.

EXAMPLE 1

Effect of Clay to Monomer Ratio on Water Absorption Capacity

NPC Alloy Preparation

Seven MCX mixtures were prepared in the amounts shown in Table 1. Clay to monomer weight ratios ranged from 0.1 to 9.62 in the seven MCX mixtures. The clay used in the MCX mixtures was NATURAL GEL™, a natural swelling clay often referred to as Wyoming bentonite, commercially available from American Colloid. The monomer was acrylamide, obtained from Cytec, West Paterson, N.J. A Control sample was made using acrylamide monomer without added clay.

Water, sodium hydroxide (NaOH), sodium bicarbonate (NaHCO$_3$), EDTA, acrylamide, N,N'-methylene bisacrylamide (NBAM) and potassium persulfate (K$_2$S$_2$O$_8$) were mixed in a 250-mL HDPE bottle. The aqueous solution was mixed well, prior to addition of clay. Clay was added and mixed again to form a homogeneous MCX mixture. All MCX mixtures were viscous but fluid before polymerization.

TABLE 1

| Component | Control | 1 | 2 | 3 | 4 | 5 | 6 | 7 |
|---|---|---|---|---|---|---|---|---|
| Water | 79.98 | 72.5 | 98.778 | 74.4 | 291.153 | 74.4 | 151.23 | 91.91 |
| NaOH | 3.768 | 3.108 | 3.904 | 2.28 | 7.498 | 1.891 | 1.563 | 0.506 |
| NaHCO$_3$ | 0.931 | 0.802 | 0.931 | 0.60 | 0.204 | 0.468 | 0.323 | 0.105 |
| EDTA | 0.109 | 0.09 | 0.116 | 0.08 | 0.217 | 0.06 | 0.042 | 0.025 |
| Acrylamide | 25.073 | 21.028 | 24.871 | 15.00 | 50.00 | 7.72 | 10.042 | 2.294 |
| NBAM | 0.057 | 0.05 | 0.058 | 0.04 | 0.123 | 0.028 | 0.022 | 0.012 |
| K$_2$S$_2$O$_8$ | 0.21 | 0.183 | 0.217 | 0.132 | 0.418 | 0.085 | 0.088 | 0.032 |
| Clay | — | 2.121 | 8.368 | 7.502 | 50.22 | 15.389 | 30.00 | 22.029 |
| Total (g) | 110.128 | 99.882 | 137.243 | 100.034 | 399.833 | 100.041 | 193.31 | 116.913 |
| Clay:Monomer Ratio (wt) | 0 | 0.10 | 0.34 | 0.50 | 1.00 | 2.00 | 3.00 | 9.60 |

The Control and MCX mixtures were left in an oven overnight at 65° C. for polymerization. After polymerization, the Control and NPC alloys were transferred to glass dishes and dried at 105° C. for 48 hours.

Water Absorption Capacity (WAC) of NPC Alloys

Approximately 1 gm of each NPC alloy and the Control was placed in a 500 mL HDPE bottle with 400 ml distilled water. After 48 hours, free water was decanted off the swollen NPC alloy using a 115 mesh screen.

The swollen NPC alloy was weighed and the water absorption capacity (WAC) was calculated according to the following equation:

$$WAC = \frac{(H_2O \text{ Swollen NPC Alloy Mass} - \text{Dried NPC Alloy Mass})}{\text{Dried NPC Alloy Mass}}$$

A projected WAC, $WAC_{prj}$, based on the Control WAC and clay content was also calculated according to the following equation:

$$WAC_{prj} = \left(\frac{\text{Parts Monomer}}{\text{Total Parts Monomer} + \text{Clay}} \times \frac{\text{Control}}{\text{WAC}}\right) + \frac{\text{Parts Clay}}{\text{Total Parts Monomer} + \text{Clay}} \times \frac{\text{Max. Est.}}{\text{Clay WAC}}$$

where the Control WAC=352 and the Maximum Estimated WAC for clay=10. For example, where a 1:3 clay to monomer ratio is used to produce the NPC alloy, the NPC alloy's $WAC_{prj}$ is [(3/4)×352]+(1/4)10=266. Likewise, where a 2:1 clay to monomer ratio is used, the NPC alloy's $WAC_{prj}$ is [(1/3)×352]+(2/3)10=124.

Finally, the monomer WAC ($WAC_m$) was also calculated to determine the water absorption capacity based on the amount of monomer used to produce the polymer/clay alloy sample being tested. The $WAC_m$ was calculated according to the following equation:

$$WAC_m = \frac{(H_2O \text{ Swollen NPC Alloy Mass} - \text{Dried NPC Alloy Mass})}{\text{Mass of Monomer used to produce NPC Alloy}}$$

The results are tabulated in Table 2.

TABLE 2

| Sample ID | | Control | 1 | 2 | 3 | 4 | 5 | 6 | 7 |
|---|---|---|---|---|---|---|---|---|---|
| Clay: Monomer Ratio | | 0.00 | 0.10 | 0.34 | 0.50 | 1.00 | 2.00 | 3.00 | 9.61 |
| WAC | g H$_2$O per g NPC alloy | 352 | 339 | 332 | 213 | 207 | 134 | 83 | 14 |
| WAC$_{prj}$ | | | 321 | 266 | 238 | 181 | 124 | 96 | 42 |
| WAC$_m$ | g H$_2$O per g monomer in NPC alloy | 421 | 441 | 472 | 364 | 414 | 403 | 349 | 250 |

As shown in Table 2, the WAC for NPC alloy Samples 1 and 2 is 339 and 332, respectively. This means that the NPC alloy absorbs 339 and 332 times its own weight in water for these two samples, respectively, versus a 352 WAC for the clay-free Control. Bentonite clay typically has a paste-like consistency up to a water absorption of 5 to 10 times its weight, after which the clay becomes dispersed in water to form a slurry. Consequently, because bentonite clay is not known as being highly water-absorbent on a per unit mass basis, as compared with a water-absorbent polymer, the drop in WAC shown in Table 2 with increasing clay to monomer ratio was a surprising and unexpected result.

For example, at a 1:1 ratio, those skilled in the art might have projected a WAC of just slightly more than 0.5× the Control's WAC because only half of the NPC alloy is networked polymer. So, taking into account the water absorption for clay alone (i.e., about 5–10), a 1:1 clay to monomer ratio in an NPC alloy would have been expected to be, at best, about ½ the Control's WAC (i.e., 176) plus 5 for the clay's expected water absorption for a $WAC_{prj}$ of 181. But Sample 4, with a 1:1 clay to monomer ratio, has a 207 WAC, which is 14.4% greater than expected. Similarly, a 2:1 clay to monomer ratio has a $WAC_{prj}$ of about 124, while Sample 5 produced a 134 WAC, which is 8.1% greater than expected. The general trend is that WAC, across a broad range of clay to monomer ratios, is substantially comparable, if not slightly improved versus the clay-free Control until a significantly high clay loading in the NPC alloy is reached. At a significantly high clay loading, it appears that the polymer loading is so low that the clay's inherent WAC is dominant.

This is a surprising and unexpected result, particularly at high clay to monomer ratios of 2:1 and 3:1. Ogawa et al ("Preparation of Montmorillonite-Polyacrylamide Intercalation Compounds and the Water Absorbing Property" *Clay Science* 7:243–251; 1989) suggest on pg. 250 that clay acts as a cross-linking agent. Thus, Ogawa et al suggest that clay would act in concert with a cross-linking agent in an MCX mixture to severely constrain a polymer formed from that mixture. Moreover, the results in Example 2 illustrate that a cross-linking agent concentration as low as about 0.1 wt. % can over cross-link a polymer, thereby substantially reducing its water absorption capacity. Thus, the sensitivity of WAC to excess cross-linking agent and Ogawa et al suggest that increasing the clay content would produce a highly constrained NPC alloy with inhibited WAC. Consequently, it is surprising and unexpected that using an MCX mixture with both a cross-linking agent and clay, for example, at a 2:1 clay to monomer ratio, would produce an NPC alloy with comparable or slightly better performance than the clay-free Control.

When calculated on the basis of an equivalent amount of acrylamide monomer used to produce an alloy, the $WAC_m$ of the polymer/clay alloys Samples 1–5 is similar to that of the Control sample. As mentioned above, monomers are more costly than clay. Thus, the $WAC_m$ results demonstrate the economic advantages of the NPC alloy.

Table 2 demonstrates that good WAC results were obtained for the composition described in Table 1 in a clay to monomer ratio of about 0.3 to about 3.0. The optimal clay to monomer ratio will depend on the intended use of the compositions falling within the scope of the claimed invention. For instance, beyond adjusting the clay to monomer ratio, as discussed more fully under Example 2, the cross-linking agent to monomer ratio can also be adjusted to increase or decrease the WAC to the desired level.

For example, as a landfill liner, a WAC for the reinforced NPC alloy composite only needs to be high enough to ensure that the NPC alloy swells sufficiently to occupy any interstitial spaces that were not occupied by NPC alloy when the composite was formed. This degree of swelling will ensure that the composite has sufficiently low permeability to water and other fluids. For example, the WAC for an NPC alloy used in a landfill liner composite could be as low as about 5. Of course, a higher WAC up to about 500 could also be used in a landfill liner composite. However, a WAC significantly much higher than 50 could reduce the structural integrity of the composite due to excess water.

Consequently, in personal care type applications, where the composite's structural integrity is likely to be a factor as well, a WAC in a range of from about 20 to about 100 would be most likely desired for the composite.

Accordingly, the above data illustrates that the unique polymer/clay alloy can provide effective water absorption for a reinforced NPC alloy composite. As well, the clay component in the NPC alloy provides a cost effective means to make a reinforced NPC alloy composite while delivering the water absorbing and/or permeability property performance desired for the intended use.

EXAMPLE 2

Effect of Cross-Linking Agent to Monomer Ratio on WAC

NPC Alloy Preparation

Three MCX mixtures were mixed in the amounts shown in Table 3. The cross-linking agent to monomer weight ratios ranged from $1.10 \times 10^{-3}$ to $9.41 \times 10^{-3}$ in the three MCX mixtures. The clay to monomer weight ratio was held constant at about 1:1. The clay used in the MCX mixtures was NATURAL GEL™. The monomer was a 1:4 (wt) mixture of acrylic acid (Aldrich) and acrylamide (Cytec).

Water, NaOH, sodium carbonate ($Na_2CO_3$), acrylic acid, acrylamide, NBAM and $K_2S_2O_8$ were mixed in the proportions shown in Table 3 in a 2-L Erlenmeyer flask. The aqueous solution was mixed well, prior to addition of clay. Clay was added and mixed again to form a homogeneous MCX mixture. All MCX mixtures were viscous but fluid before polymerization.

TABLE 3

| | Sample (g) | | |
|---|---|---|---|
| Component | 8 | 9 | 10 |
| Water | 1000 | 1000 | 1000 |
| NaOH | 10 | 10 | 10 |
| $Na_2CO_3$ | 12 | 12 | 12 |
| Acrylic Acid (M) | 20 | 20 | 20 |
| Acrylamide (AM) | 80 | 80 | 80 |
| NBAM | 0.941 | 0.303 | 0.11 |
| $K_2S_2O_8$ | 0.6 | 0.6 | 0.6 |
| Clay | 99 | 105 | 105 |
| Total (g) | 1222.541 | 1227.903 | 1227.71 |
| NBAM/(AA + AM) Wt Ratio ($\times 10^3$) | 9.41 | 3.03 | 1.10 |

The MCX mixtures were left in an oven overnight at 65° C. for polymerization. After polymerization, the NPC alloys were transferred to glass dishes and dried at 105° C. for 48 hours.

Water Absorption Capacity (WAC) of Polymer/Clay Alloys

Approximately 1 gm of NPC alloy Sample 8 was placed in a 500 mL HDPE bottle with 400 ml distilled water. After 48 hours, free water was decanted off the swollen NPC alloy using a 115 mesh screen.

The swollen NPC alloy was weighed and the water absorption capacity (WAC) was calculated as described in Example 1. Samples 9 and 10 were treated in the same manner. The results are tabulated in Table 4.

The monomer WAC ($WAC_m$) was also calculated to determine the water absorption capacity based on the amount of monomer used to produce the NPC alloy sample being tested. These results are also tabulated in Table 4.

TABLE 4

| Sample | | 8 | 9 | 10 |
|---|---|---|---|---|
| NBAM/(AA + AM) Wt Ratio ($\times 10^3$) | | 9.41 | 3.03 | 1.10 |
| WAC | g $H_2O$ per g polymer/clay alloy | 145 | 281 | 281 |
| $WAC_m$ | g $H_2O$ per g monomer in polymer/clay alloy | 324 | 641 | 640 |

As shown in Table 4, the NPC alloy's WAC increases as the cross-linking agent to monomer ratio decreases from 9.41×10⁻³ to 3.03×10⁻³. However, it is believed that a further significant decrease in cross-linking agent to monomer ratio (e.g., to about 0.10×10⁻³) would sufficiently reduce the mechanical strength of the NPC alloy's networked polymer and thereby limit NPC alloy's ability to absorb and retain water.

Of course, to the extent the polymer is not cross-linked, the polymer will dissolve in water. Also, at low levels of cross-linking, the polymer may fracture and become water-soluble. However, if the degree of cross-linking is too high, there is too much constraint on the polymer and its water absorption capacity is reduced.

Accordingly, the above data illustrates that the unique NPC alloy can provide effective water absorption for a reinforced NPC alloy composite. As well, controlling the cross-linking agent to monomer ratio, alone or in combination with the clay to monomer ratio, provides a means for designing the water absorbing and/or permeability property performance desired for the composite's intended use.

EXAMPLE 3

Hydraulic Conductivity of Reinforced Networked Polymer Clay Alloy Composite

Monomer/Clay Mixture Preparation

Two MCX mixtures were prepared in the amounts shown in Table 5. The clay to monomer weight ratios were 1:1 and 2:1 in Samples 11 and 12, respectively. The clay used in the MCX mixtures was NATURAL GEL™. The monomer was acrylamide.

Water, NaOH, NaHCO₃, EDTA, acrylamide, NBAM and $K_2S_2O_8$ were mixed in the proportions shown in Table 5 in a 2-L Erlenmeyer flask. The aqueous solution was mixed well, prior to addition of clay. Clay was added and mixed again to form a homogeneous MCX mixture. The MCX mixtures were viscous but fluid before being contacted with the reinforcing agent.

TABLE 5

| Component | 11 (g) | 12 (g) |
|---|---|---|
| Water | 291.153 | 74.4 |
| NaOH | 7.498 | 1.891 |
| NaHCO₃ | 0.204 | 0.468 |
| EDTA | 0.217 | 0.06 |
| Acrylamide | 50.00 | 7.72 |
| NBAM | 0.123 | 0.028 |
| K₂S₂O₈ | 0.418 | 0.085 |
| Clay | 50.22 | 15.389 |
| Total (g) | 399.833 | 100.041 |
| Clay to Monomer Ratio (wt) | 1.00 | 1.99 |

Reinforced NPC Alloy Composite Preparation

PETROMAT™ 4597 and AMOCO 4551™ (Amoco) geotextiles were used as reinforcing agent. These commercially available geotextiles are nonwoven fabrics comprising polypropylene fibers. The unit weight for PETROMAT™ 4597 and AMOCO 4551™ is 0.14 kg/m² and 0.2 kg/m², respectively. The geotextiles were about 1–3 mm thick. The thickness typically varies in a non-woven geotextile and it is difficult to measure because of the fibers.

Reinforced Sample A1 was prepared by pouring Sample 11 MCX mixture in a thickness of about 2.5 mm thickness onto a 20 cm×20 cm piece of PETROMAT™ 4597 geotextile, representing a loading of about 2.5 kg/m². The MCX mixture was intimately distributed in and on the geotextile material using a wooden rolling pin.

Reinforced Sample A2 was prepared in the same manner as Sample A1 using Sample 12 MCX mixture and AMOCO 4551™ geotextile.

Reinforced Sample A3 was prepared using Sample 11 MCX mixture and two layers of AMOCO 4551™ geotextile. The MCX mixture was poured onto one layer of geotextile (i.e., bottom layer) and then covered with the second layer of geotextile (i.e., top layer). The MCX mixture was intimately distributed in and on both layers using a wooden rolling pin, though the mixture was primarily substantially embedded throughout the bottom layer.

The reinforced MCX mixture samples was placed between two glass plates and put into an oven at 75° C. for 2 hours for polymerization. Spacers were placed between the glass plates so that the polymerized samples would be of substantially uniform thickness, without added pressure during polymerization. The glass plates also reduced evaporation of MCX mixture components during polymerization.

Reinforced Samples A1 and A2 were dried in an oven at 80° C. overnight. Sample A3 was not dried, but was stored in a polyethylene bag directly after polymerization. Though Samples A1 and A2 were dried, it is preferable to use the reinforced NPC alloy composite in an non-dried state, as in Sample A3.

Hydraulic Conductivity Test

The rate of water flow through a layer of the reinforced NPC alloy composite samples under a hydraulic gradient was measured using ASTM 5887-95.

ASTM 5887-95 is a standard method to measure the flux or flow of water per unit area through the sample. The test specimen was set up in a flexible wall permeameter, subjected to a total stress of 550 kPa and a back pressure of 515 kPa for a period of 48 hours. Flow of deionized water was initiated by raising the pressure on the influent side of the test specimen to 530 kPa. This places an effective confining stress on the specimen of approximately 20 kPa. All samples were tested at 20 kPa, except Sample A2, which was tested at 120 kPa. The flux was determined when inflow and outflow were approximately equal.

Because the sample's thickness has an influence on its hydraulic conductivity, the flux determined by the ASTM 5887-95 test was used to calculate hydraulic conductivity based on each sample's different thickness. The hydraulic conductivity results in Table 7 were calculated as follows:

$$k/\mu = (Q/A)(\Delta L/\Delta p)$$

$$K = \rho g(k/\mu)$$

where k is permeability, $\mu$ is fluid viscosity, (Q/A) is flux, ($\Delta L/\Delta p$) is the reciprocal of the pressure gradient, which accounts for variations in the sample's thickness and thereby normalizes $k/\mu$ and hence K, K is hydraulic conductivity, $\rho$ is fluid density and g is a gravitational constant.

In addition, the change in specimen thickness was measured and used to calculate the percentage of swelling during the test.

The results of the hydraulic conductivity tests are tabulated in Table 7. BENTOMAT® ST (CETCO, Arlington, Ill.) was used as a comparative sample. BENTOMAT® ST is a GCL consisting of a sodium bentonite layer (approximately 4.9 kg/m²) between woven and non-woven geotextiles, which are needle-punched together.

The initial and final thicknesses are shown in Table 7 as $T_0$ and $T_f$, respectively. The unit weight shown in Table 7 for Samples A1 and A2 is on a moisture-free basis. Sample A3 was not dried after polymerization and, therefore, the exact loading on a moisture-free basis is not known. However, it is estimated that the unit weight on a moisture-free basis is less than 0.75 kg/m².

For convenience, the MCX mixture and geotextile used in each sample is summarized in Table 6.

TABLE 6

| Sample | Reinforcing Agent | Monomer/Clay Mixture |
|---|---|---|
| A1 | PETROMAT 4597 | 11 |
| A2 | AMOCO 4551 | 12 |
| A3 | Double AMOCO 4551 | 11 |
| Comparative | BENTOMAT ST | N/A |

TABLE 7

| Sample | Weight (kg/m²) | $T_o$ (mm) | $T_f$ (mm) | Swell (%) | $\sigma_{effective}$ (kPa) | Flux (m³/m²/s) | K (cm/s) |
|---|---|---|---|---|---|---|---|
| A1 | 0.64 | 1.08 | 4.80 | 344 | 20 | $4.8 \times 10^{-9}$ | $1.5 \times 10^{-9}$ |
| A2 | 0.96 | 1.70 | 2.19 | 29 | 120 | $3.7 \times 10^{-9}$ | $5.1 \times 10^{-10}$ |
| A3 | <0.75 | 3.89 | 6.92 | 78 | 20 | $1.6 \times 10^{-9}$ | $7.2 \times 10^{-10}$ |
| Comparative | 4.90 | 6.20 | 8.68 | 40 | 20 | $3.2 \times 10^{-9}$ | $2.0 \times 10^{-9}$ |

The water flux through Samples A1 and A3 was similar to the flux through the comparative sample at an effective confining stress of 20 kPa. Even at this very low NPC alloy loading (as little as 0.64 kg/m², where the weight of the NPC alloy is calculated on a water-free basis), the reinforced composite is as effective as GCL with 4.9 kg/m² bentonite. The average hydraulic conductivity (K) for Samples A1 and A3 of $1.1 \times 10^{-9}$ cm/s, which is about a 50% improvement versus the comparative sample's K of $2.0 \times 10^{-9}$ cm/s. This improved K value is particularly significant since hydraulic conductivity tends to increase as the confining stress approaches zero, as discussed more fully in Example 5. However, this data demonstrates the composite's surprising and unexpected ability to deliver relatively consistent hydraulic conductivity performance under both lower confining stress and higher confining stress conditions.

The flux through Sample A2 was tested at a confining stress of 120 kPa to determine the effect of the confining stress on flux and corresponding hydraulic conductivity. The flux through Sample A2 was similar to the flux through Samples A1 and A3 and the hydraulic conductivity was similar to Sample A3. Accordingly, there was little change when the confining stress was increased from 20 kPa to 120 kPa.

Accordingly, the reinforced NPC alloy composite provides a hydraulic conductivity performance at least comparable to, if not better than, conventional GCL, but weighing substantially less than GCL and having a dramatically improved clay retention capacity versus GCL when exposed to water. In turn, this contributes significantly to the composite's long-term hydraulic conductivity performance, which will remain relatively stable over long-term and persistent water exposure in the environment. Meanwhile, under similar environmental conditions, the hydraulic-conductivity for GCL will deteriorate over time as clay particles migrate through the GCL fabric layer as discussed more fully under Example 8.

EXAMPLE 4

One Alternative Preparation of Reinforced Networked Polymer Clay Alloy Composite Reinforced NPC Alloy Composite Preparation Reinforced Samples B1 and B2 were prepared in the same manner as Reinforced Sample A3 in Example 3 using Sample 11 MCX mixture (see Example 3) and 2 layers of AMOCO 4551™ geotextile. The geotextile material was intimately contacted with the MCX mixture using a TEFLON™ coated piston, with pressure applied by hand, until the mixture was substantially distributed throughout the material. It appeared that the MCX mixture was more evenly distributed using the piston, as compared with the wooden rolling pin used in Example 3.

The reinforced MCX mixture samples was placed in an oven at 65° C. for 2 hours for polymerization.

The reinforced samples were stored in a polyethylene bag directly after polymerization.

Hydraulic Conductivity Test

The test procedures for hydraulic conductivity measurement were the same as those in Example 3. The results are tabulated in Table 8 with the results for the same comparative sample used in Example 3.

TABLE 8

| Sample | Weight (kg/m²) | $T_0$ (mm) | Swell (%) | $\sigma_{effective}$ (kPa) | Flux (m³/m²/s) | K (cm/s) |
|---|---|---|---|---|---|---|
| B1 | <0.75 | 3.61 | 112 | 20 | $2.7 \times 10^{-9}$ | $1.4 \times 10^{-9}$ |
| B2 | <0.75 | 3.67 | 114 | 20 | $3.0 \times 10^{-9}$ | $1.6 \times 10^{-9}$ |
| Comparative | 4.90 | 6.20 | 40 | 20 | $3.2 \times 10^{-9}$ | $2.0 \times 10^{-9}$ |

The water flux and K through samples B1 and B2 was similar to the flux and K through the comparative sample at an effective confining stress of 20 kPa. Even at this very low NPC alloy loading (<0.75 kg/m², where the weight of the NPC alloy is calculated on a water-free basis), the reinforced composite is as effective as GCL with 4.9 kg/m² bentonite (dry weight).

Accordingly, the reinforced NPC alloy composite provides a hydraulic conductivity performance at least comparable to, if not better than, conventional GCL, but weighing substantially less than GCL and having a dramatically improved clay retention capacity versus GCL when exposed to water. In turn, this contributes significantly to the composite's long-term hydraulic conductivity performance, which will remain relatively stable over long-term and persistent water exposure in the environment. Meanwhile, under similar environmental conditions, the hydraulic conductivity for GCL will deteriorate over time as clay particles migrate through the GCL fabric layer as discussed more fully under Example 8.

EXAMPLE 5

Flux at Zero Confining Stress

Sample Preparation

Samples were prepared using the following MCX mixture having a clay to monomer ratio of 2:1:

100.8 g (1.52 wt. %) acrylic acid 400.5 g (6.04 wt. %) acrylamide 55.1 g (0.83 wt. %) NaOH
51.5 g (0.78 wt. %) $Na_2CO_3$
1.62 g (0.02 wt. %) NBAM
12.8 g (0.19 wt. %) potassium persulfate
1000.8 g (15.09 wt. %) clay
5009.9 g (75.53 wt. %) water Reinforced NPC alloy composites were prepared using the MCX mixture and TERRAFIX® 270R-A geotextile.

Samples were prepared in a semi-continuous process, as discussed above and illustrated in FIG. 3, to distribute the MCX mixture in the geotextile and form the composite. The MCX mixture was applied to the geotextile as described below for each set of samples. A polyethylene film cover sheet was placed on top of the MCX mixture and a vacuum was applied to the sample from the geotextile's opposing side. The MCX mixture was intimately distributed in and on the geotextile material by applying the vacuum. The cover sheet reduced channeling through the sample and the MCX mixture was more evenly distributed through the geotextile, as compared with a sample prepared without a cover sheet.

For Samples 13 and 14, the MCX mixture was poured in a thickness of about 3.5 mm onto a 0.95 m×0.97 m piece of geotextile. A second layer of the geotextile was placed on top of the MCX mixture. A polyethylene film cover sheet was placed on top of the second geotextile layer and a vacuum pressure of about 20 kPa was applied to the opposing side of the first geotextile layer.

For Samples 15 and 16, the MCX mixture was poured in a thickness of about 2.5 mm onto a 0.95 m×0.50 m piece of geotextile. A polyethylene film cover sheet was placed on top of the MCX mixture and a vacuum pressure of about 16 kPa was applied to the geotextile's opposing side.

Samples 17 and 18 were prepared substantially the same as Samples 15 and 16, but using a vacuum pressure of about 15 kPa, instead of 16 kPa.

All samples were heated in the semi-continuous process using a CATA-DYNE™ infrared heater (placed about 500 mm above the sample) at a temperature of about 80° C. for 10 minutes to form the reinforced NPC alloy composite.

Samples were cut into 9.0 cm discs using a high speed drill cutter and weighed. The results are presented in Table 9.

TABLE 9

| Sample | Unit Weight (kg/m²) |
| --- | --- |
| 13 | 3.47 |
| 14 | 2.92 |
| 15 | 2.73 |
| 16 | 2.90 |
| 17 | 2.42 |
| 18 | 2.46 |

Hydraulic Conductivity Tests

The hydraulic conductivity tests used to evaluate Samples 13–18 were based on a modified ASTM 5887-95 test. The apparatus used for the test was a Baroid filter press. Compressed air was used to apply pressure through a pressure manifold. Unlike ASTM 5887-95, under this hydraulic conductivity test, no confining stress was applied to the sample. As mentioned previously, the hydraulic conductivity of a liner will generally decrease with increase confining stress. Accordingly, the hydraulic conductivities illustrated in this example, with zero confining stress applied, represents a "worst case scenerio" where the linear may, at least early in its life, be exposed to confining stresses that are low or near zero.

The samples were placed at the bottom of the filter apparatus followed by a rubber gasket, cell and cap. The assembly was inserted into the support stand, sealed by tightening a "T" screw and then connected to the pressure manifold. The test fluid was then introduced to the cell and the sample was pre-soaked in the test fluid for 2 hours at atmospheric pressure.

After 2 hours, a flow pressure of 15 kPa was applied. Effluent was weighed, at an interval of minutes at the beginning of test and several hours thereafter.

The amount of effluent was used to calculate the flux through the sample, using an effective flow are of 7.7 cm diameter.

In this example, deionized water was used as the test fluid.

The water flux through the samples was measured at 48 hours. These water flux results are presented in Table 10.

TABLE 10

| Sample | Water Flux @ 48 hours (m³/m²/s) | Projected Hydraulic Conductivity Based on | |
| --- | --- | --- | --- |
| | | 2 mm Thickness | 6 mm Thickness |
| 13 | $4.87 \times 10^{-9}$ | $6.36 \times 10^{-10}$ | $1.91 \times 10^{-9}$ |
| 14 | $6.44 \times 10^{-9}$ | $8.41 \times 10^{-10}$ | $2.52 \times 10^{-9}$ |
| 15 | $5.59 \times 10^{-9}$ | $7.31 \times 10^{-10}$ | $2.19 \times 10^{-9}$ |
| 16 | $4.78 \times 10^{-9}$ | $6.24 \times 10^{-10}$ | $1.87 \times 10^{-9}$ |
| 17 | $3.85 \times 10^{-9}$ | $5.03 \times 10^{-10}$ | $1.51 \times 10^{-9}$ |
| 18 | $5.86 \times 10^{-9}$ | $7.65 \times 10^{-10}$ | $2.30 \times 10^{-9}$ |

As demonstrated in Table 10, the water flux through Samples 13 through 18 using deionized water at zero confining stress are similar to the results for the reinforced NPC alloy composite samples tested in Example 6 (salt water, zero confining stress), Example 3 (deionized water, 20 kPa and 120 kPa confining stress) and Example 4 (deionized water, 20 kPa confining stress).

In contrast, the hydraulic conductivity for water through conventional GCL's is significantly increased as the confining stress is reduced. Moreover, as mentioned in the discussion in Example 6, the salt water flux through GCL is known to be much greater than $1 \times 10^{-8}$ m³/m²/s. Several conventional GCL's were tested with fresh water in a paper by D.E. Daniel ("Geosynthetic clay liners, part two: hydraulic properties" *Geotechemical Fabrics Report* 14:5:22; June-July, 1996). At a confining stress range from 100 to 1000 kPa, conventional GCL's have a hydraulic conductivity range from $3 \times 10^{-10}$ to $1 \times 10^{-9}$ cm/s. The hydraulic conductivity increases to a range from $6 \times 10^{-10}$ to $6 \times 10^{-9}$ cm/s when the confining stress ranges from 10 to 100 kPa. Only one data point was provided for a confining stress under 10 kPa. The hydraulic conductivity was $2 \times 10^{-9}$ cm/s for a confining stress of 7 kPa. The data was extrapolated to show a hydraulic conductivity range of from $6 \times 10^{-9}$ cm/s to about $1 \times 10^{-7}$ cm/s, when the confining stress is decreased to 1 kPa. Accordingly, conventional GCL's have a hydraulic conductivity at least $1 \times 10^{-7}$ cm/s or greater, thereby making the composite hydraulic conductivity test results of about $2.5 \times 10^{-9}$ cm/s, at zero confining stress, particularly surprising and unexpected.

EXAMPLE 6

Salt Water Flux Tests

One problem, among others, with conventional barrier liners, such as GCL, is that their hydraulic barrier properties diminish with exposure to salt water, particularly salt water having a salt concentration about 3 wt. % or greater. For example, a conventional GCL has a flux of about $1\times10^{-8}$ $m^3/m^2/s$, using tap water. However, salt water flux through GCL is known to be much greater than $1\times10^{-8}$ $M^3/m^2/s$, for example from about $1\times10^{-7}$ $m^3/m^2/s$ to about $1\times10^{-6}$ $m^3/m^2/s$. This example demonstrates how a reinforced NPC alloy composite substantially maintains its low permeability on exposure to salt water.

Sample Preparation

Samples 19 and 24 were prepared using the following MCX mixture (2:1 clay to monomer ratio) applied in the semi-continuous process described in Example 5

100.8 g (1.52 wt. %) acrylic acid 400.5 g (6.04 wt. %) acrylamide 55.1 g (0.83 wt. %) NaOH 51.5 g (0.78 wt. %) $Na_2CO_3$ 1.62 g (0.02 wt. %) NBAM 12.8 g (0.19 wt. %) potassium persulfate 1000.8 g (15.09 wt. %) clay 5009.9 g (75.53 wt. %) water Samples 20 to 23 were prepared using the following MCX mixture (2:1 clay to monomer ratio), which is substantially similar to Samples 19 and 24 but in a smaller batch size and applied in a batch type process described below:

50.9 g (1.54 wt. %) acrylic acid 200.5 g (6.05 wt. %) acrylamide 27.55 g (0.83 wt. %) NaOH 25.8 g (0.78 wt. %) $Na_2CO_3$ 0.81 g (0.02 wt. %) NBAM 6.48 g (0.19 wt. %) potassium persulfate 500 g (15.09 wt. %) clay 2502 g (75.50 wt. %) water Reinforced NPC alloy composites were prepared using the MCX mixtures described above and TERRAFIX® 270R-A geotextile, a non-woven polypropylene fiber geotextile, having a thickness of about 2.0–2.5 mm.

For Samples 20–23, a 2 mm thickness MCX mixture was poured onto a 120 mm diameter piece of the geotextile. A polyethylene film cover sheet was placed on top of the MCX mixture and a vacuum pressure in the range of from about 16 to about 30 kPa was applied to the sample from the opposing side of the geotextile. The MCX mixture was intimately distributed in and on the geotextile material by applying the vacuum. The cover sheet reduced channeling through the sample and the MCX mixture was more evenly distributed through the geotextile, as compared with a sample prepared without a cover sheet.

The samples were heated using two 320 W infrared lamps (placed about 250 mm above the sample) at a temperature of about 80° C. for 10 minutes to polymerize the MCX mixture.

Samples 19 and 24 were similarly prepared. However, the vacuum process was applied in the semi-continuous process, described in Example 5 and then passed under the CATA-DYNE™ infrared heater.

Samples were cut into 9.0 cm discs using a high speed drill cutter and weighed. The results are presented in Table 11.

TABLE 11

| Sample | Weight (g) | Unit Weight $(kg/m^2)$ |
|---|---|---|
| 19 | 13.6 | 2.14 |
| 20 | 19.06 | 3.00 |

TABLE 11-continued

| Sample | Weight (g) | Unit Weight $(kg/m^2)$ |
|---|---|---|
| 21 | 15.01 | 2.36 |
| 22 | 23.26 | 3.66 |
| 23 | 19.4 | 3.05 |
| 24 | 15.6 | 2.45 |

Hydraulic Conductivity Tests

The hydraulic conductivity tests were based on the ASTM 5887-95 test, described in Example 5.

Flux was tested using two different solutions. The first solution was a 3.5 wt. % NaCl solution. The second solution was an artificial seawater having the following composition: 0.46 M NaCl, 0.035 M $MgSO_4$, and 0.01 M KCl. The artificial seawater composition is similar to a natural seawater composition suggested in *Introduction to Geochemistry* (K. B. Krauskopf, McGraw-Hill, pg. 324; 1967).

Figure 4:
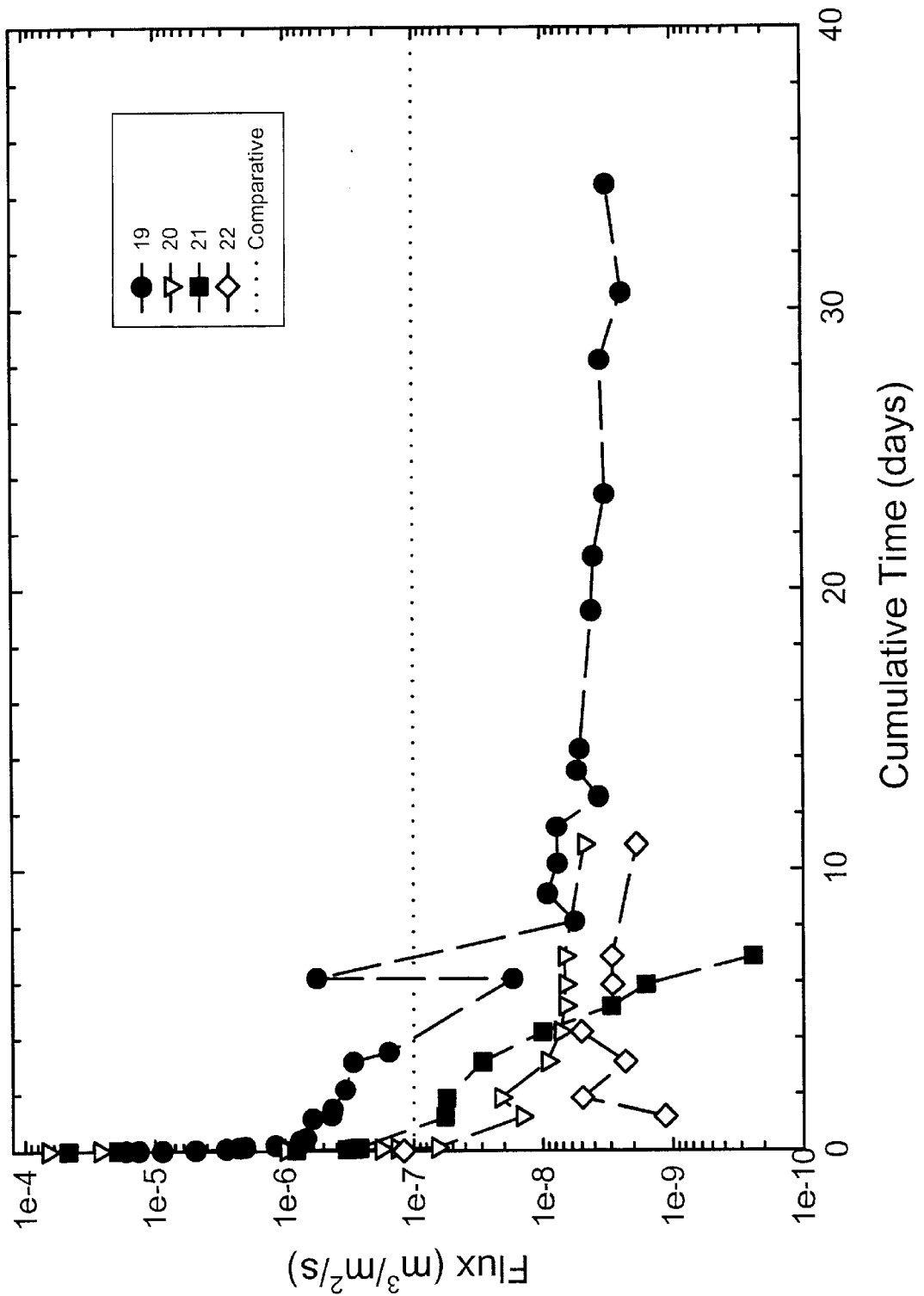
FIG. 4 is a graphical representation of the results of the flux test in Example 6 for 3.5% (wt.) NaCl solution and the minimum flux for conventional GCL under similar salt water conditions indicated by the dotted line.
Figure 5:
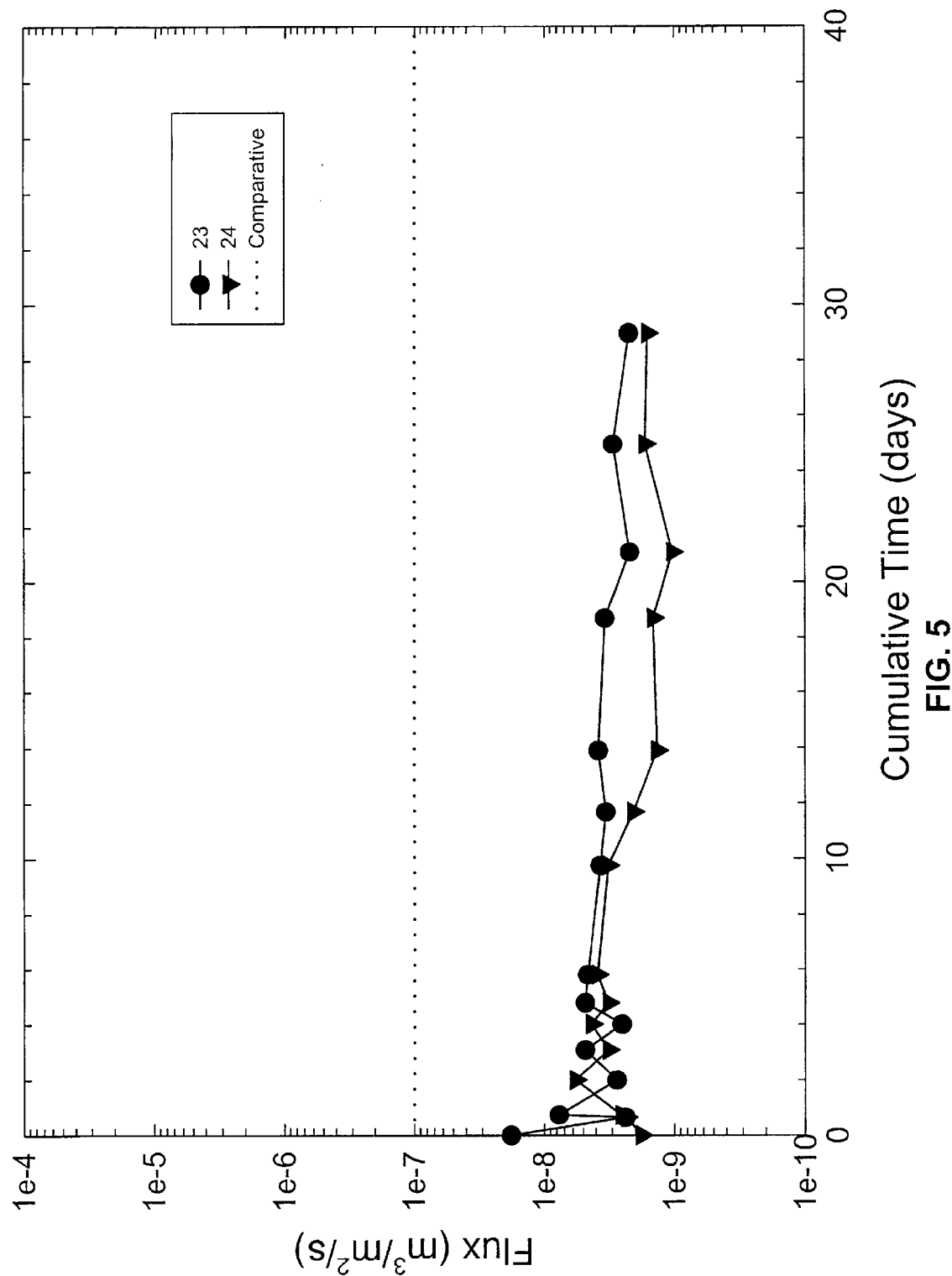
FIG. 5 is a graphical representation of the results of the flux test in Example 6 for artificial seawater and the minimum flux for conventional GCL under similar salt water conditions indicated by the dotted line.
Figure 6:
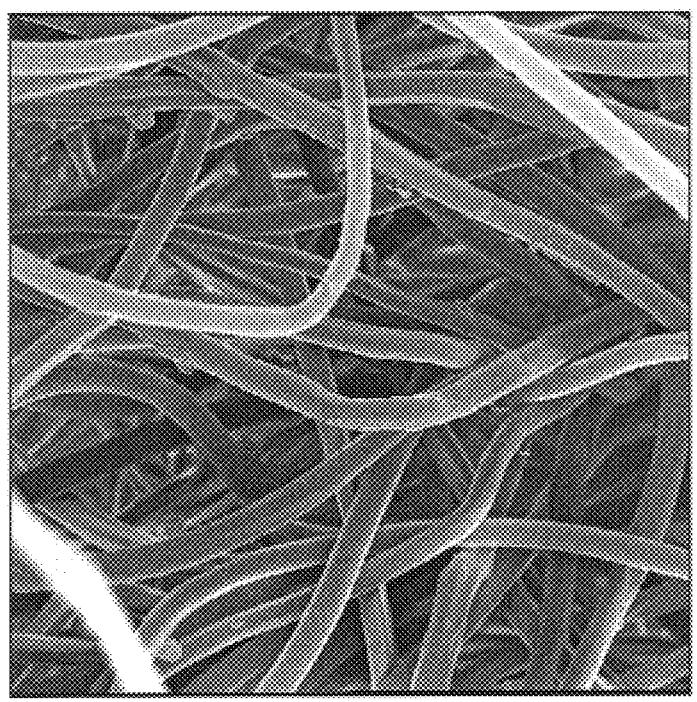
FIG. 6 is a scanning electron microscope (SEM) micrograph of a top plan perspective of the reinforcing agent used in Example 7, at a magnification of 140×.

The results of the flux tests for the 3.5% NaCl solution and the artificial seawater solution are presented graphically in FIGS. 4 and 5, respectively.

As shown in FIG. 4, the 3.5 wt % NaCl solution's flux through Samples 19, 20, 21 and 22 dropped dramatically and rapidly within the first day of testing. In fact, the first several hours of test results produced the most dramatic decrease in flux. Accordingly, there are multiple data points shown near time zero for these samples. However, the lowest flux data points near time zero on the y-axis, in units of $m^3/m^2/s$, for samples 19, 20, 21 and 22 are $1\times10^{-6}$, $6\times10^{-8}$, $4\times10^{-7}$ and $1.5\times10^{-7}$, respectively. As a reference point, the dotted line drawn at $1\times10^{-7}$ $m^3/m^2/s$ indicates the lowest flux expected from a conventional GCL clay based liner when exposed to a similar salt solution. In fact, many conventional GCL's are reasonably expected to have a salt water flux significantly greater than $1\times10^{-7}$ $m^3/m^2/s$, which is at least one order of magnitude greater than the average salt water flux shown for the composite samples of the invention after about 5 days of salt water exposure. This substantial disparity in the salt water flux performance between the conventional GCL compositions and the reinforced NPC alloy composite is both surprising and unexpected. Without being bound by theory, it is believed that the unique physicochemical properties of the NPC alloy may provide some synergistic interaction between the clay and networked polymer, which, as discussed more fully under Example 7, is preferably in a naturally hydrated state from date of manufacture and thereby accounts for the composite's precipitous flux drop in the first several hours as well as its at least one, if not two, order of magnitude improvement in long term salt water flux performance.

As shown in FIG. 5, the initial seawater flux results, in units of $m^3/m^2/s$, for Samples 23 and 24 are $2\times10^{-8}$ and about $2\times10^{-9}$, respectively, which are significantly less than for Samples 19–22. Again, as a reference point, the dotted line drawn at $1\times10^{-7}$ $m^3/m^2/s$ indicates the lowest flux expected from a conventional GCL clay based liner when exposed to a similar salt solution. This substantial disparity in the seawater flux performance between the conventional GCL compositions and the reinforced NPC alloy composite is both surprising and unexpected, for the reasons stated above.

EXAMPLE 7

SEM and X-Ray Analysis

The following SEM micrographs and X-ray analyses illustrate that (1) clay in the NPC alloy is chemically associated with the polymer, (2) clay does not become dissociated from the NPC alloy when the polymer is swollen, (3) NPC alloy is intimately integrated with the reinforcing agent in the reinforced NPC alloy composite, and (4) the reinforced NPC alloy composite can contain a significant amount of occluded water retained from manufacture.

Monomer/Clay Mixture Preparation

An MCX mixture was prepared as shown in Table 12. The clay used in the MCX mixture was NATURAL GEL™. The monomer was a 1:4 (wt) mixture of acrylic acid (Aldrich) and acrylamide (Cytec).

Water, NaOH, NaHCO$_3$, acrylic acid, acrylamide, NBAM and K$_2$S$_2$O$_8$ were mixed in a 10-L HDPE pail. The aqueous solution was mixed well, prior to addition of clay. Clay was added and mixed again to form a homogeneous MCX mixture. The MCX mixture was viscous but fluid before polymerization.

TABLE 12

| Component | Amount (g) |
| --- | --- |
| Water | 5009.9 |
| NaOH | 55.1 |
| NaHCO$_3$ | 51.5 |
| Acrylic Acid | 100.8 |
| Acrylamide | 400.5 |
| NBAM | 1.62 |
| K$_2$S$_2$O$_8$ | 12.8 |
| Clay | 1000.8 |
| Total (g) | 6633.02 |
| Clay to Monomer Ratio (wt) | 2.00 |

Reinforced NPC Alloy Composite Preparation

The MCX mixture was poured in a thickness of about 1.5 mm onto a 0.95 m×0.80 m piece of TERRAFIX® 270R-A geotextile, as a reinforcing agent. A polyethylene cover sheet was placed on top of the MCX mixture and a vacuum pressure in a range of from about 16 to about 30 kPa was applied to the sample from the geotextile's opposing side. The MCX mixture was intimately distributed in and on the geotextile material by applying the vacuum.

The reinforced MCX mixture sample was put under an infrared heater at 80° C. for 8 minutes for polymerization. The moisture content of the reinforced NPC alloy composite was about 75%.

Scanning Electron Microscopy (SEM)

The reinforced NPC alloy composite was examined using a JEOL Model No. JSM 6301 FXV Scanning Electron Microscope (SEM, Japan Electron Optics Limited, Japan) at the SEM Facility, Department of Earth & Atmospheric Sciences, University of Alberta, Edmonton, Alberta, Canada.

Samples were pretreated for SEM examination by placing the samples in a holder and immersing them in liquid nitrogen (i.e., about −196° C.). Once frozen, the samples were removed from the liquid nitrogen, using pliers or a knife, quickly torn or cut, as indicated below, to obtain a cross-sectional perspective of the sample. The samples were then quickly transferred to the SEM vacuum chamber, where they were warmed to −40° C. to sublime any surface ice crystals. Next, the samples were placed in a coating chamber where a thin layer of gold was applied to the sample to increase electrical conductivity. The samples were then returned to the SEM vacuum chamber for examination. The samples were maintained at or near liquid nitrogen temperature during the gold coating and subsequent SEM examination. This was done so that the structure of the sample would be preserved. The samples contained considerable moisture and thus had to be maintained in a frozen state for the SEM to operate properly.

Figure 7:
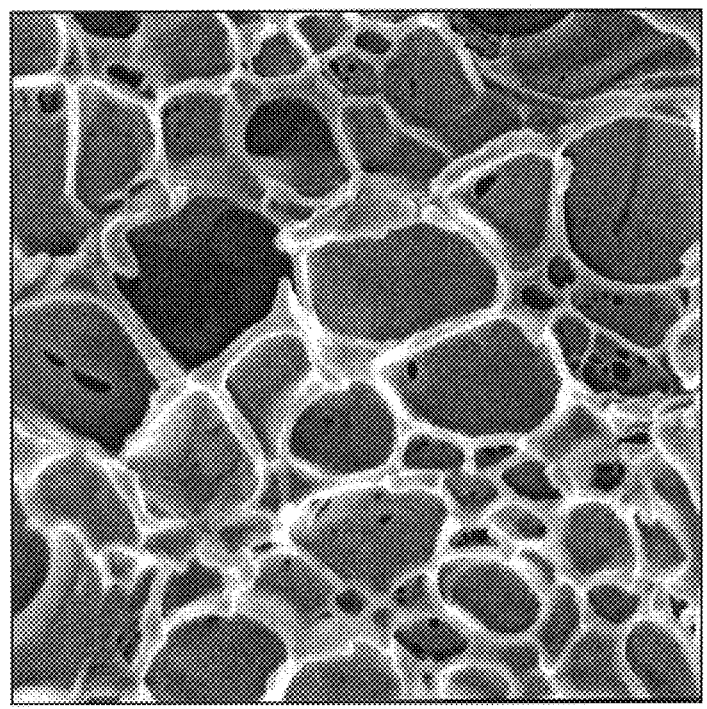
FIG. 7 is an SEM micrograph of a hydrated polymer used for comparison in Example 7, at a magnification of 7000×.
Figure 8:
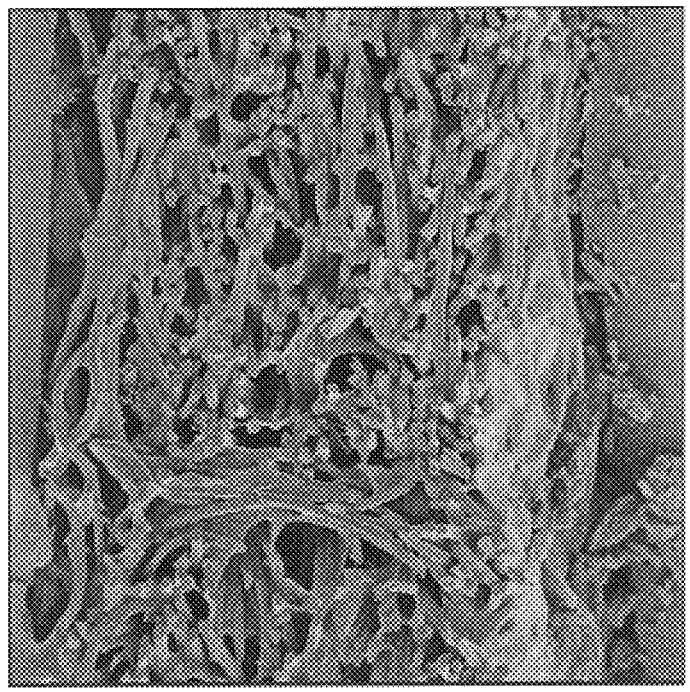
FIG. 8 is an SEM micrograph of a cross-section of a reinforced networked polymer/clay alloy composite produced in Example 7, at a magnification of 50×.
Figure 9:
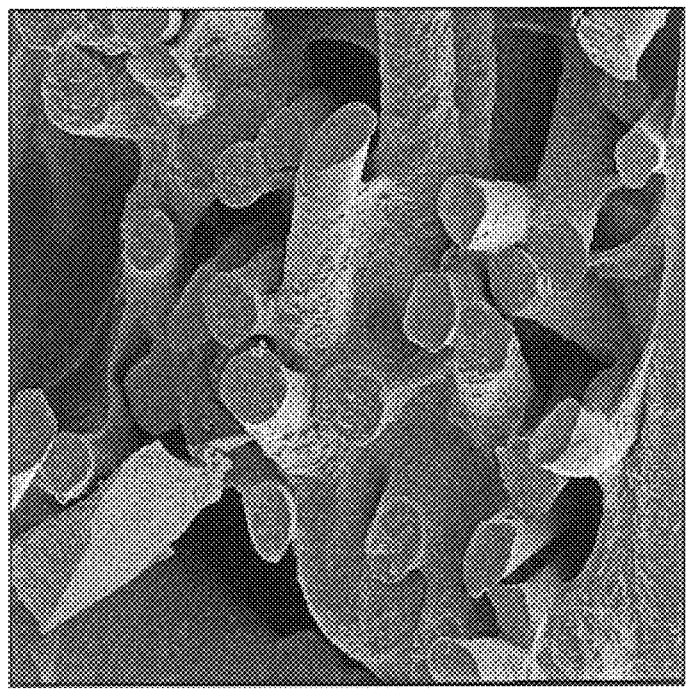
FIG. 9 is an SEM micrograph of a cross-section of a reinforced networked polymer/clay alloy composite produced in Example 7, at a magnification of 270×.
Figure 10:
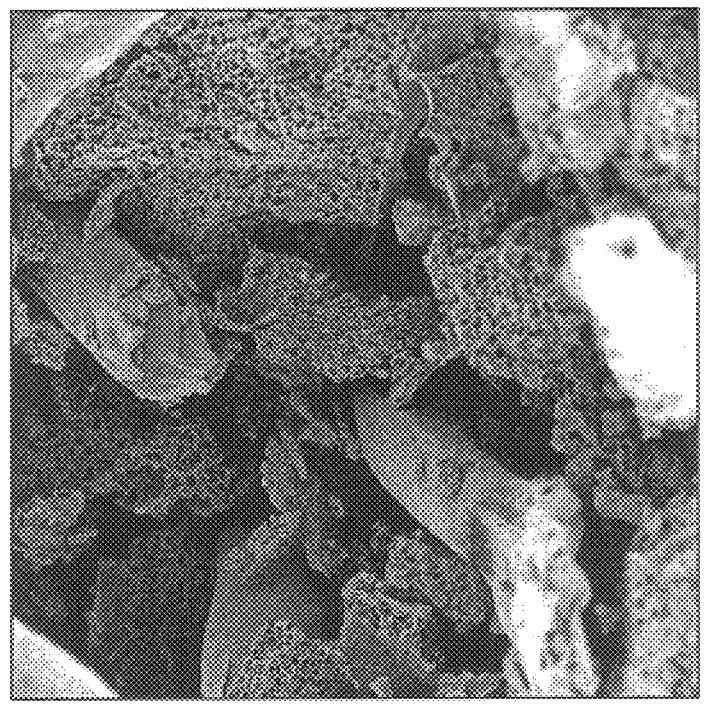
FIG. 10 is an SEM micrograph of a cross-section of a water-swelled reinforced networked polymer/clay alloy composite produced in Example 7, at a magnification of 500×.
Figure 11:
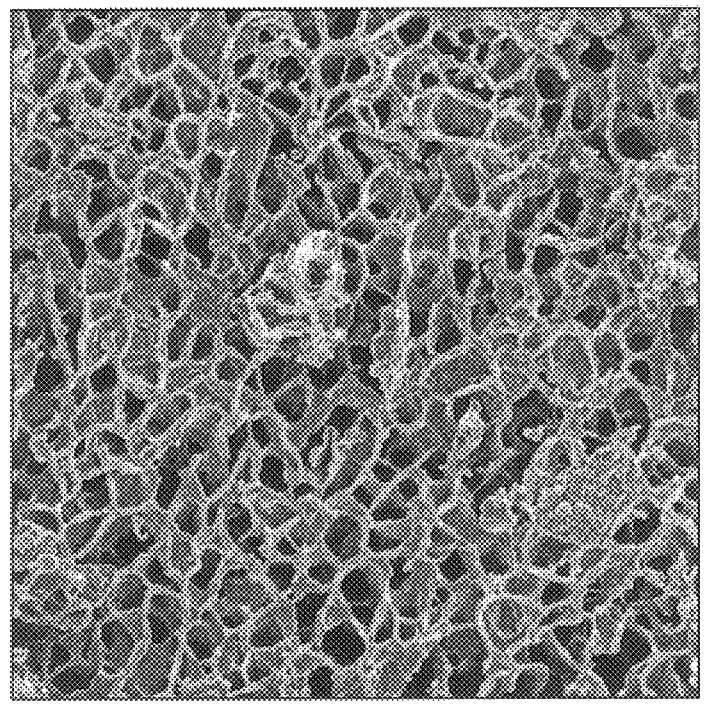
FIG. 11 is an SEM micrograph of a cross-section of a water-swelled reinforced networked polymer/clay alloy composite produced in Example 7, at a magnification of 4500×.

The sample in FIGS. 8 and 9 was cut with a knife prior to mounting. Both micrographs show the cut edges of fibers of the reinforcing agent. Particles seen in FIG. 9 are fragments from the cutting step in preparing the sample for SEM examination. The sample in FIGS. 10 and 11 was severed with a pair of pliers, instead of a knife, prior to mounting. FIG. 10 shows the fractured edges of fibers of the reinforcing agent and other fragments produced by fracturing. The SEM micrographs of FIGS. 6 to 12 are discussed in Table 13.

Discussion of SEM Micrographs

In summary, the SEM micrographs illustrate that (1) clay in the NPC alloy is chemically associated with the polymer, (2) clay does not become dissociated from the NPC alloy when the polymer is swollen, (3) NPC alloy is intimately integrated with the reinforcing agent in the reinforced NPC alloy composite and (4) the reinforced NPC alloy composite can contain a significant amount of occluded water retained from manufacture.

TABLE 13

| FIG. # | Magnification | Description | Observations |
| --- | --- | --- | --- |
| 6 | 140X | Comparative. Top plan perspective of reinforcing agent without NPC alloy. | |
| 7 | 7000X | Comparative. Potassium acrylate cross-linked and polymerized without clay. No reinforcing agent. Sample immersed in water for 10 minutes prior to SEM. | Swollen polymer has crater-like open-cell structure. The open cells were previously occupied by occluded water, which was removed by SEM pre-treatment procedures. It is expected that acrylamide/sodium acrylate copolymer would behave in a similar manner. |
| 8 | 50X | Reinforced NPC alloy composite. Sample dried from the original 75 wt. % moisture to about 25–50 wt. % with ambient drying conditions over a 2 week period. The NPC alloy shrank around the reinforcing agent fibers. The | Illustrates NPC alloy intimately integrated with reinforcing agent. Also illustrates thin layer of NPC alloy (right-hand side of micrograph) integrated with NPC alloy in reinforcing agent; i.e., not a laminate structure. |

TABLE 13-continued

| FIG. # | Magnification | Description | Observations |
|---|---|---|---|
| | | shrinkage indicates the volume occupied by previously occluded water. | |
| 9 | 270X | Same as FIG. 8 | No individual clay particles can be seen in the SEM micrographs, illustrating that the clay particles are chemically associated with polymer in NPC alloy, even at clay to monomer ratio of 2:1. |
| 10 | 500X | Reinforced NPC alloy composite immersed in water for 10 minutes prior to SEM. | Illustrates how swollen NPC alloy expands to conform to and substantially occupy interstitial spaces in reinforcing agent. |
| 11 | 4500X | Same as FIG. 10. | Illustrates that clay particles are chemically associated with polymer in NPC alloy. No free clay particles are seen, therefore indicating that the clay does not dissociate from NPC alloy when water-swollen. Swollen NPC alloy has open-cell structure, similar to polymer without clay (FIG. 7). Also, the degree of occluded water is substantially similar to polymer without clay (FIG. 7), therefore indicating that clay even at high loading does not have a disproportionately detrimental effect on NPC alloy's swelling capacity versus a clay-free water absorbing polymer. |
| 12 | 650X | Comparative. Same monomer/cross-linking agent mixture as used for FIG. 10 sample, but without clay. Immersed in water for 10 minutes prior to SEM. | Swollen polymer fills interstitial spaces in reinforcing agent in same manner as NPC alloy in FIG. 10 Open-cell structure of polymer without clay similar to that of the clay-based sample shown in FIG. 10. Comparison to FIG. 10 illustrates how the clay is (a) integrated in the NPC alloy and (b) does not have a disproportionately detrimental effect on NPC alloy's swelling capacity. |

Figure 12:
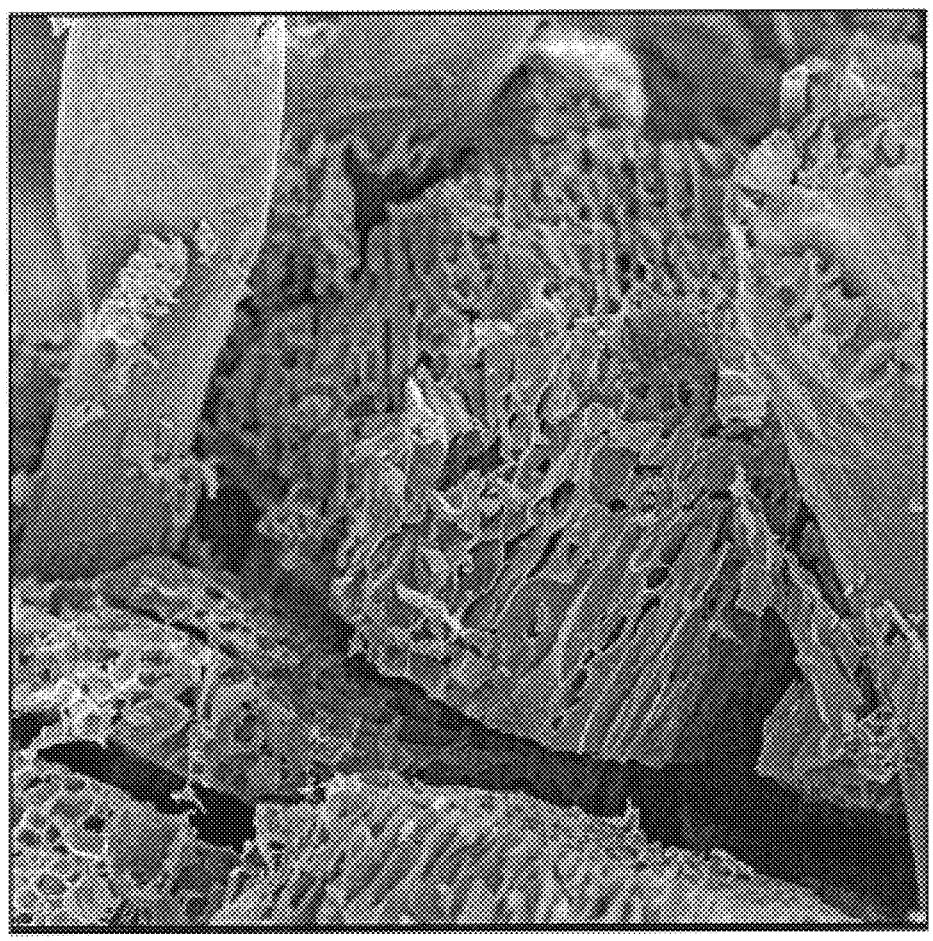
FIG. 12 is an SEM micrograph of a cross-section of a water-swelled polymer, without clay, at a magnification of 650×.

As shown more clearly in the comparison between FIG. 10 (reinforced NPC alloy composite) and FIG. 7 (swollen polymer without clay) or FIG. 12 (swollen polymer without clay in reinforcing agent), the swollen NPC alloy open-cell structure is similar to that of clay-free polymers. Accordingly, the clay does not constrain the NPC alloy's water swelling capacity. In view of Ogawa et al (discussed more fully in Example 1), which suggests that clay acts as a cross-linking agent for making water absorbent polymers, this is a surprising and unexpected result. Also, in view of the cross-linking agent results in Example 2, which illustrate that a cross-linking agent concentration as low as about 0.1 wt. % can over cross-link a polymer, thereby substantially reducing its water absorption capacity, these results are most particularly surprising and unexpected at a relatively high clay to monomer ratio of 2:1.

X-Ray Analyses

The Energy Dispersive X-Ray (EDX) analysis device of the SEM collects signals from an area of 1 $\mu$m×1 $\mu$m at a penetration depth of about 1 $\mu$m. X-ray analysis was conducted at numerous sites on the sample in FIG. 11, including the NPC alloy at the center of FIG. 11. Consistently at each site, peaks appeared for gold (2.1, 8.5 keV), silicon (1.74 keV), aluminum (1.49 keV), sodium (1.04 keV), magnesium (1.25 keV), and iron (0.615, 6.40 keV). The gold peak was a result of the gold treatment for the SEM examination. The relative strengths and positions of the silicon and aluminum peaks in the EDX spectra were consistent with those expected for bentonite clay. All sites examined showed the presence of silicon, aluminum, sodium, magnesium and iron. This analysis shows that the NPC alloy is homogeneous throughout the sample, even at the 1 $\mu$m$^3$ level. Accordingly, the clay in the NPC alloy is chemically associated with the polymer.

EXAMPLE 8

Clay Migration Tests

This example illustrates that, when the reinforced NPC alloy composite is immersed in water, the NPC alloy swells with substantially no clay separating from the composite.

Reinforced NPC Alloy Composite

An MCX mixture was prepared by mixing 40.51 g acrylic acid with 500 g water. 36.6 potassium hydroxide and 0.624 g NBAM were then added with stirring. After the potassium hydroxide was in solution, 24.39 g potassium carbonate was dissolved, followed by addition of 160.33 g acrylamide, 4.83 g potassium persulfate and 500 g water. 594.07 g of the monomer mixture was blended with 199.79 g bentonite clay in a flood blender to give a creamy suspension.

A layer of the MCX mixture was poured onto a 2 cm×2 cm piece of TERRAFIX® 270R-A geotextile. The MCX mixture was intimately distributed in and on the geotextile material by hand. The MCX mixture was polymerized in the reinforcing agent by heating in a 75° C. oven for 8 minutes.

This reinforced NPC composite was labeled as Sample A in the clay migration tests.

Comparative Sample B—No Polymerization Initiator, No Cross-linking Agent

The monomer/clay mixture for Comparative Sample B was prepared by mixing 18.7 g acrylic acid, 6.1 g sodium hydroxide, 34.9 g clay and 18 g water to form a viscous paste. The paste was then forced into a 2 cm×2 cm piece of TERRAFIX® 270R-A. The monomer/clay mixture could not be embedded into the geotextile at 100 kPa. So, one of the inventors, weighing about 80 kg, placed a piece of PLEXIGLAS™ on top of the sample and stood on it while rocking back and forth. About half of the monomer/clay mixture was forced into the fabric using this method. No polymerization initiator or cross-linking agent was added to the monomer/clay mixture.

The sample was dried in an oven at 75° C. for one hour.

Comparative Sample C—No Polymerization Initiator

A monomer/clay mixture was prepared by mixing 79.89 g acrylamide, 20.56 g acrylic acid, 0.3 g NBAM as cross-linking agent, 9.995 sodium hydroxide, 9.962 g sodium carbonate, and 1000 g water. 552.8 g of the monomer mixture was blended with 100.55 g bentonite clay in a flood blender to give a creamy suspension. No polymerization initiator was added to the monomer/clay mixture.

A layer of the monomer/clay mixture was poured onto a 2 cm×2 cm piece of TERRAFIX® 270R-A geotextile. The mixture was intimately distributed in and on the geotextile material by hand. The monomer/clay mixture was heated in a 70° C. oven for 1 hour in the reinforcing agent.

This sample was labeled as Sample C in the clay migration tests.

Comparative Sample D—Pre-formed Oligomer (MW 2,000)

Comparative Sample D was prepared by mixing 6.5 g pre-formed polyacrylic acid, 1.6 g sodium hydroxide, 26 g water and 10.70 g clay. The polyacrylic acid, having a molecular weight of 2,000, was obtained from Aldrich Chemical Co.

A layer of the pre-formed oligomer/clay mixture was poured onto a 2 cm×2 cm piece of TERRAFIX® 270R-A geotextile. The pre-formed oligomer/clay mixture was intimately distributed in and on the geotextile material by hand. The sample was dried in an oven at 75° C. for one hour.

Comparative Sample E—Pre-formed Polymer (MW 450,000)

Comparative Sample E was prepared by mixing 4.74 g pre-formed polyacrylic acid, 1.44 g sodium hydroxide, 96 g water and 11.52 g clay. The polyacrylic acid, having a molecular weight of 450,000, was obtained from Aldrich Chemical Co.

A layer of the pre-formed polymer/clay mixture was poured onto a 2 cm×2 cm piece of TERRAFIX® 270R-A geotextile. The mixture was intimately distributed in and on the geotextile material using a wooden rolling pin. The sample was dried in an oven at 75° C. for one hour.

Comparative Commercial Products

Two commercial products were also tested for comparative purposes in the clay migration tests.

GUNDSEAL® (GSE Lining Technology, Inc., Houston, Tex.) is a bentonite clay/polyethylene geomembrane liner. Sodium bentonite is adhered to a polyethylene geomembrane using an adhesive at a loading of 1 lb/ft$^2$ (4.9 kg/m$^2$). The sample was about 3 mm thick. A 2.5 cm×2.5 cm piece of GUNDSEAL® was labeled as Comparative Sample F.

BENTOMAT® DN (CETCO, Arlington, Ill.) is a geosynthetic clay liner consisting of a sodium bentonite layer between two layers of geotextile, which are needle-punched together. A 2.5 cm×2.5 cm piece of BENTOMAT® DN was labeled as Comparative Sample G.

Clay Migration Test Procedure

Each of the samples was placed in a glass bottle. 100 mL deionized water at room temperature (about 20° C.) were then poured into the bottle.

The bottle was left standing without disturbance at room temperature. The sample was observed at 3 hours and 22 hours after addition of water, as described in Table 14.

TABLE 14

| Sample | Description of Sample | Observations |
| --- | --- | --- |
| A | MCX mixture: acrylamide, sodium acrylate, cross-linking agent, persulfate polymerization initiator, and clay. The MCX mixture was pressed into the fabric and polymerized in a fabric @ 75° C. for 8 minutes. | After 3 hours, the sample had swelled considerably. After 22 hours, there was some additional swelling of the NPC alloy. The swelled NPC alloy was puffy in appearance. Both the fabric and clay remained as an integral part of the NPC alloy. (see FIGS. 13A and 13B). Substantially no clay separated from the NPC alloy after 22 hours of immersion time. |
| B | Comparative. Monomer/clay mixture: acrylic acid, NaOH, water and clay. No polymerization initiator or cross-linking agent was used. The monomer/clay mixture was pressed into a fabric and dried @ 75° C. for one hour. | After 3 hours, the acrylic acid and sodium acrylate dissolved in the water. The clay had migrated off the fabric and swelled at the bottom of the test bottle. There was no change after 22 hours. |
| C | Comparative. Monomer/clay mixture: acrylamide, acrylic acid, NaOH, NBAM (cross-linking agent), water and clay. No polymerization initiator was used. The monomer/clay mixture was pressed into a fabric and heated for one hour @ 70° C. | After 3 hours, the acrylamide and sodium acrylate dissolved in the water. The clay had migrated off the fabric and dispersed in the water. There was no change after 22 hours. |
| D | Comparative. A pre-formed polyacrylic acid (MW = 2000) was mixed with clay and pressed into the fabric. | After 3 hours, the polyacrylic acid dissolved in the water. The clay migrated off the fabric and dispersed in the water. There was no change after 22 hours. (see FIG. 14A and 14B) |
| E | Comparative. A pre-formed polyacrylic acid (MW = 450,000) | After 3 hours, the polyacrylic acid dissolved in the water and some clay |

TABLE 14-continued

| Sample | Description of Sample | Observations |
|---|---|---|
| | was mixed with clay and pressed into a fabric | had migrated off the fabric. After 22 hours, the remaining clay had migrated off the fabric and swelled at the bottom of the bottle. |
| F | Comparative. GUNDSEAL ® | After 3 hours, the clay had migrated off the backing material and started to swell. After 22 hours, the clay was more swollen. |
| G | Comparative. BENTOMAT ® DN | After 3 hours, the clay had migrated from between the two geotextile layers and dispersed into the water. The clay had swelled and settled in the bottom of the bottle by 22 hours. (see FIGS. 15A and 15B) |

Line drawings were prepared from some of the photographs taken during the clay migration tests summarized in Table 14.

Figure 13B:
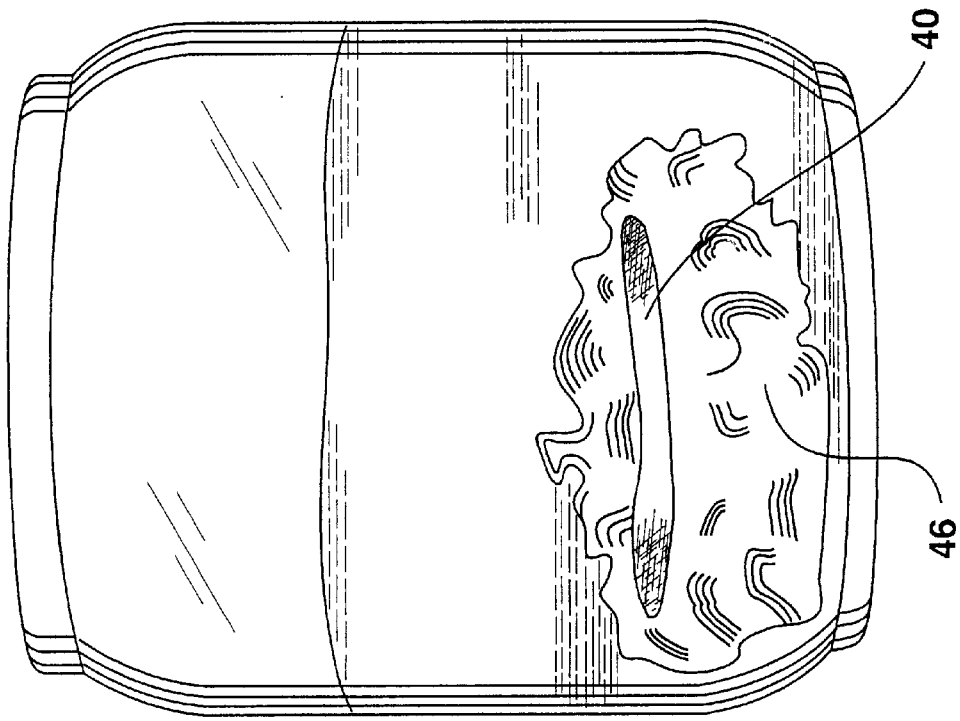
FIGS. 13A and 13B are drawings based on photographs taken of Sample A in Example 8 prior to immersion (13A) and after 3 hours immersion in deionized water (13B)
Figure 13A:
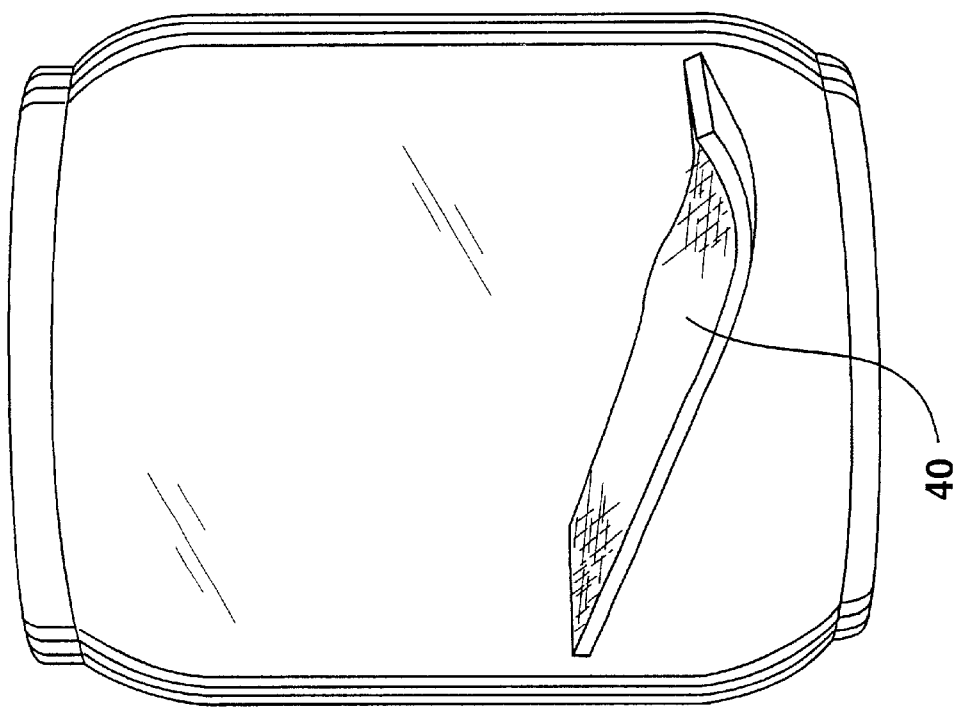

Sample A was a reinforced NPC alloy composite. FIG. 13A illustrates Sample A prior to immersion in deionized water. The NPC alloy is in the reinforcing agent 40. FIG. 13B illustrates the sample after 3 hours immersion in deionized water. The swelled NPC alloy 46 had a puffy appearance. Substantially no clay separated from the composite. Also, the swelled NPC alloy 46 was still integrated with the reinforcing agent 40.

Figure 14B:
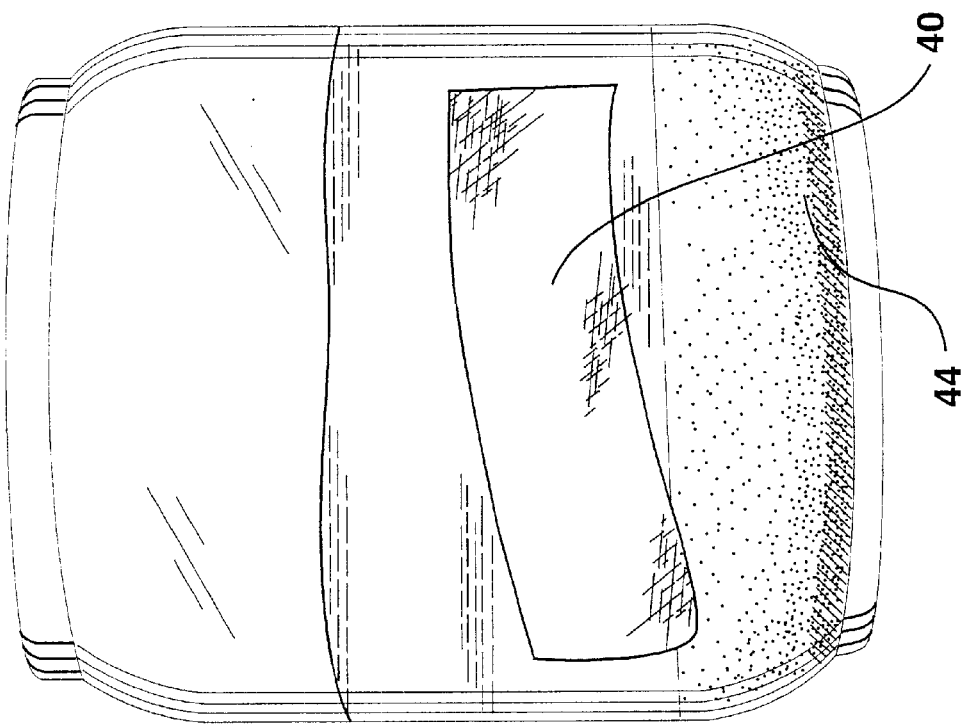
FIGS. 14A and 14B are drawings based on photographs taken of Sample D in Example 8 prior to immersion (14A) and after 3 hours immersion in deionized water (14B)
Figure 14A:
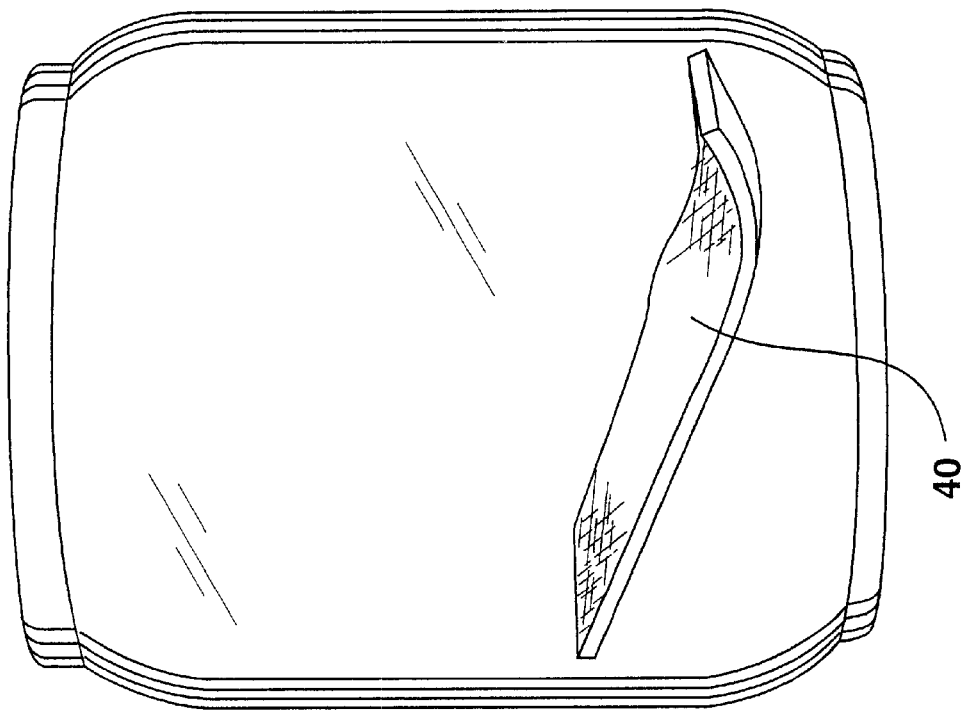

FIG. 14A illustrates Comparative Sample D prior to immersion in deionized water. The pre-formed polymer and clay mixture is in the reinforcing agent 40. FIG. 14B illustrates the sample after 3 hours immersion in deionized water. The polymer had dissolved in water and the clay 44 migrated off the reinforcing agent 40 and dispersed in the water. Some settling of the clay 44 is observed at the bottom of the bottle.

Figure 15B:
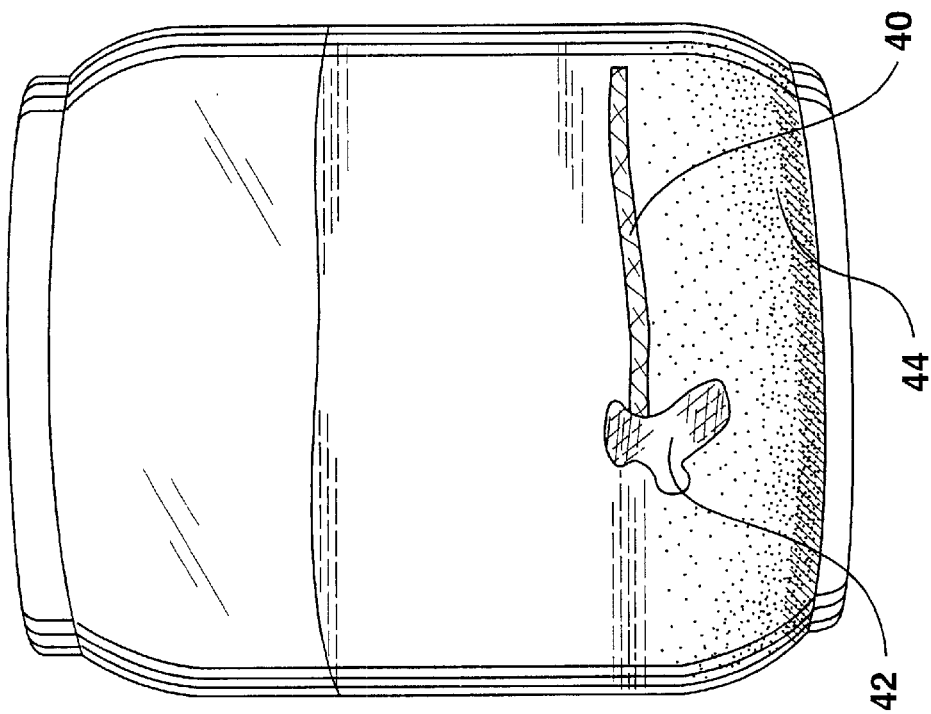
FIGS. 15A and 15B are drawings based on photographs taken of Sample G in Example 8 prior to immersion (15A) and after 3 hours immersion in deionized water (15B).
Figure 15A:
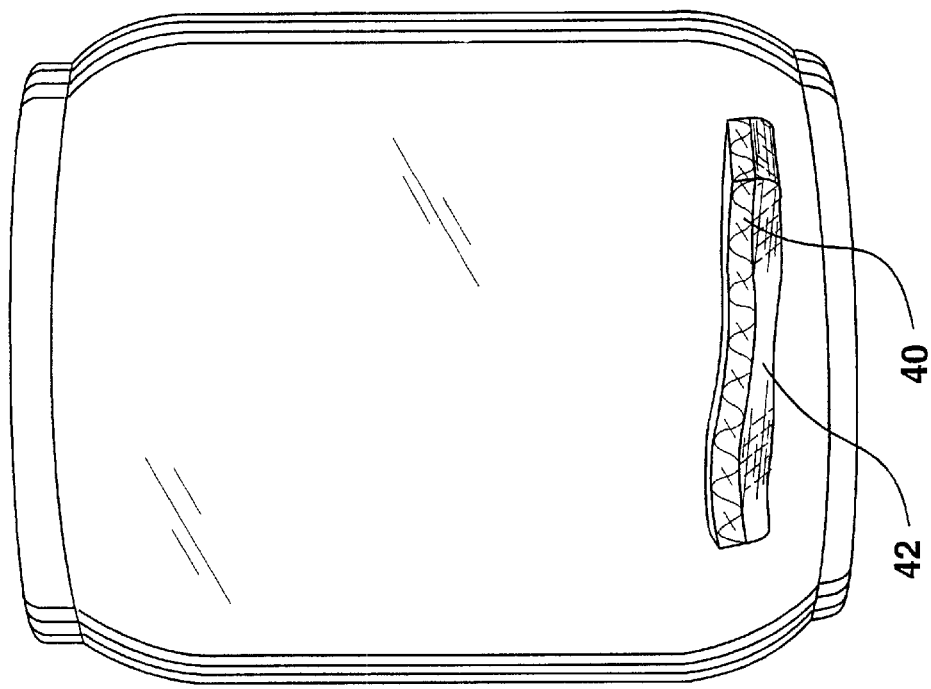

FIG. 15 illustrates Comparative Sample G prior to immersion in deionized water. The sample has clay sandwiched between a first reinforcing agent 40 and a second reinforcing agent 42. FIG. 15B illustrates the sample after 3 hours immersion in deionized water. The clay 44 had migrated from between the two reinforcing agent layers 40, 42 and dispersed into the water. The clay 44 of Sample G had settled more densely than the clay of Comparative Sample D, shown in FIG. 14B.

The results in Table 14 and FIG. 13B illustrate how the clay is an integral part of the NPC alloy. Moreover, the results demonstrate how the NPC alloy is an integral part of the composite. In all of the comparative samples, clay migrates from the mixture and/or the reinforcing agent. Also, monomer and pre-formed polymer mixture migrate from the reinforcing agent. This is shown more clearly in FIGS. 14B and 15B.

The reinforced NPC alloy composite remains substantially intact on exposure to deionized water at about 20° C. Specifically, substantially no clay separates from the NPC alloy. Moreover, the composite is expected to exhibit substantially similar performance in deionized water in a temperature range of about 1° C. to about 60° C. This represents a significant improvement over the conventional techniques.

EXAMPLE 9

Residual Monomer Content

One concern about using acrylamide as a monomer for preparing an NPC alloy is the leaching of any residual monomer. The FDA limit for leachable acrylamide in polyacrylamide is 0.05% (500 ppm, 500 µg/g) when the polyacrylamide is used in treatment of potable water and for paper and paperboard for food contact applications (EPA/600/X-85/270 July 1985, PB88-170824).

This example provides residual monomer data for a polymer and an NPC alloy. Generally, the amount of residual monomer is dependent on initiator concentration, reaction time, and reaction temperature. For example, residual monomer content generally decreases with increased temperature, increased reaction time and increased initiator concentration.

Sample Preparation

A monomer mixture was prepared by mixing 20 g acrylic acid, 80 g acrylamide, 10 g sodium hydroxide, 12 g sodium carbonate, and 0.6 g potassium persulfate in 1000 mL water. The monomer mixture was divided into three parts and NBAM was added as a cross-linking agent at 0.1%, 0.3% and 0.9%, by weight, respectively. Each of the three monomer mixtures was sub-divided into three parts. Clay was added to some of the mixtures in an amount of about 1:1 monomer to clay or about 1:2 monomer to clay, as shown in Table 15. The MCX mixtures were blended in a food blender to produce a smooth, homogeneous mixture.

Samples of the monomer and MCX mixtures were transferred to plastic beakers and placed in an 80° C. oven for one hour for polymerization. The samples were removed from the oven and allowed to cool to room temperature. The samples were dried at 95° C. for a couple of days.

Residual Monomer Analysis

The residual acrylamide monomer was analyzed by EPA Method 8316 entitled "Acrylonitrile, Acrylamide and Acrolein by High Performance Liquid Chromatography (HPLC)."

A weighed sample of dried polymer or polymer/clay alloy (1–2 g) was placed in a polyethylene beaker with about 200 mL water and allowed to stand overnight at room temperature (about 20°) overnight. The polymer and NPC alloy samples swelled and absorbed some of the water. The remaining water was decanted from each swollen polymer and NPC alloy and analyzed for acrylamide content. The results are presented in Table 15.

TABLE 15

| Sample | Monomer Mixture (wt.) | Monomer:Clay (wt.) | Leached Acrylamide ppm (µg/g polymer) |
|---|---|---|---|
| 25 | 20% Acrylic Acid, 80% Acrylamide, 0.1% NBAM | No Clay | 13.1 |
| 26 | 20% Acrylic Acid, 80% Acrylamide, 0.3% NBAM | No Clay | 128 |
| 27 | 20% Acrylic Acid, 80% Acrylamide, 0.9% NBAM | No Clay | 22 |
| 28 | 20% Acrylic Acid, 80% Acrylamide, 0.3% NBAM | 1:1 | 108 |
| 29 | 20% Acrylic Acid, 80% Acrylamide, 0.9% NBAM | 1:1 | 7596 |
| 30 | 20% Acrylic Acid, 80% Acrylamide, 0.3% NBAM | 1:2 | 90.1 |

The amount of leached acrylamide, leached by water from the dried polymer and NPC alloy samples, was well below the FDA limit of 500 ppm for all samples except one. Sample 29 resulted in a very high leached acrylamide concentration. Because of the inordinately high residual monomer, it appears that Sample 29 did not polymerize properly. Thus, Sample 29 is an aberrant data point, especially in view of the Sample 28 result, based also on a 1:1 MCX mixture, but with only 108 ppm residual acrylamide, and the Sample 26 result, a clay-free, monomer, cross-linking agent mixture, but with only 128 ppm residual acrylamide.

It was expected that polymerization may not proceed as extensively and, therefore, the amount of leached acrylamide would be greater, for samples containing clay, especially at higher amounts of clay. Surprisingly, however, as shown in Table 15, the amount of leached acrylamide was similar for Samples 28 and 30 (0.3% NBAM, 1:1 and 1:2 monomer to clay, respectively) and Sample 26 (0.3% NBAM, no clay). It is expected that the residual monomer contents will be similar for reinforced NPC alloy composite samples.

This and the other examples presented herein demonstrates the advantages of the reinforced NPC alloy composite over conventional GCL's used in fluid barrier applications and water absorbency applications.

Preferred compositions and processes for practicing the invention have been described. It will be understood that the foregoing is illustrative only and that other embodiments of the process for producing a reinforced NPC alloy composite can be employed without departing from the true scope of the invention defined in the following claims.

What is claimed is:

1. A process for producing a reinforced networked polymer/clay alloy composite, comprising the steps of:
   (a) preparing a monomer/clay mixture by mixing at least a monomer, clay particles, a cross-linking agent, and a mixing fluid in a vessel;
   (b) contacting the monomer/clay mixture and a reinforcing agent;
   (c) exposing the monomer/clay mixture to a polymerization initiator means; and
   (d) polymerizing the monomer/clay mixture in the presence of the reinforcing agent so that a reinforced networked polymer/clay alloy composite is formed.

2. The process of claim 1, wherein the reinforcing agent comprises a substrate having a porous structure and the contacting step includes distributing the monomer/clay mixture on and in the substrate, so that a substantial portion of the porous structure is occupied by the monomer/clay mixture.

3. The process of claim 2, wherein the substrate is selected from the group consisting of knitted, woven and non-woven, natural and synthetic fibers.

4. The process of claim 3, wherein the synthetic fibers are selected from the group consisting of polypropylene, polyester, polyamide, polyethylene fibers, and combinations thereof.

5. The process of claim 2, further comprising a substantially non-porous layer attached to a side of the substrate opposite the side on which the monomer/clay mixture is distributed.

6. The process of claim 5, wherein the substantially non-porous layer is formed of a polymer selected from the group consisting of HDPE, PVC, VFPE, fPP, CSPE, and combinations thereof.

7. The process of claim 2, wherein the monomer/clay mixture is distributed on and in the porous substrate by vibration, rolling, scrubbing, spraying, hydraulic loading, pressure, vacuum, and combinations thereof.

8. The process of claim 1, wherein the reinforcing agent comprises non-aggregated fibers and the contacting step includes mixing the reinforcing agent into the monomer/clay mixture.

9. The process of claim 8, wherein the monomer/clay/fiber mixture is distributed in a mold prior to polymerizing.

10. The process of claim 8, wherein the non-aggregated fibers are selected from the group consisting of polypropylene, polyester, polyamide, polyethylene fibers, and combinations thereof.

11. The process of claim 1, wherein the polymerization initiator means is selected from the group consisting of a chemical substance, electromagnetic radiation having a wavelength less than about 10 nm, and combinations thereof.

12. The process of claim 11, wherein the chemical substance is selected from the group consisting of free radical initiators, carbanions, carbonium ions, and combinations thereof.

13. The process of claim 12, wherein the free radical initiator is selected from the group consisting of (a) alkali metal salts of sulfite, bisulfite, persulfate and benzoyl peroxide; (b) ammonium salts of sulfite, bisulfite, persulfate and benzoyl peroxide; (c) 2,2'-azobis(2-amidino-propane)-dihydrochloride and 2,2'-azobis(4-cyanopentanoic acid); and combinations thereof.

14. The process of claim 1, wherein the mixing fluid is selected from the group consisting of water, alcohol, organic solvents, and combinations thereof.

15. The process of claim 1, wherein the clay particles are swelling clay particles selected from the group consisting of montmorillonite, saponite, nontronite, laponite, beidellite, iron-saponite, hectorite, sauconite, stevensite, vermiculite and combinations thereof.

16. The process of claim 1, wherein the clay particles are non-swelling clay particles selected from the group consisting of kaolin minerals, serpentine minerals, mica minerals, chlorite minerals, sepiolite, palygorskite, bauxite, silica and combinations thereof.

17. The process of claim 1, wherein the weight ratio of clay to monomer in the monomer/clay mixture is in a range of from about 0.05:1 to about 19:1.

18. The process of claim 1, wherein the weight ratio of clay to monomer in the monomer/clay mixture is in a range of from about 0.5:1 to about 3:1.

19. The process of claim 1, wherein the monomer has the following general formula:

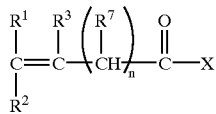

wherein X is selected from the group consisting of OM, $OR^4$ and $NR^5R^6$, M is an alkali or alkaline earth metal ion or $NH_4^+$, $R^1$, $R^2$, $R^3$, $R^5$, $R^6$ and $R^7$ are independently selected from the group consisting of H, $CH_3$, $CH_2CH_3$, $CH_2CH_2CH_3$, $CH(CH_3)_2$, $CH_2CH_2CH_2CH_3$, and CN, and $OR^4$ is selected from the group consisting of OH, $OCH_3$, $OCH_2CH_3$, $OCH_2CH_2CH_3$, $OCH(CH_3)_2$, $OCH_2CH_2CH_2CH_3$, $OCH_2CH_2OH$ and $(OCH_2CH_2)_mOH$, n=0 to about 10 and m=1 to about 10.

20. The process of claim 1, wherein the monomer is selected from the group consisting of acrylic acid, acrylamide, sodium acrylate, potassium acrylate, methacrylic acid, isopropylacrylamide, and combinations thereof.

21. The process of claim 1, wherein the cross-linking agent is selected from the group consisting of N,N'-methylene bisacrylamide, phenol formaldehyde, terephthalaldehyde, allylmethacrylate, diethyleneglycol diacrylate, ethoxylated trimethylolpropane triacrylate, ethylene carbonate, ethylene glycol diglycidal ether, tetraallyloxyethane, triallylamine, trimethylolpropanetriacrylate, and combinations thereof.

22. A product produced by the process according to any one of the preceding claims.

23. A reinforced networked polymer/clay alloy composite produced by the process of claim 1, comprising a networked polymer/clay alloy, wherein the alloy is a chemically integrated composition of polymer and clay, and the alloy is intimately integrated with a reinforcing agent so that, when the composite is immersed in deionized water, at a temperature in a range of from about 20° C. to about 30° C., the alloy swells with substantially no clay separating from the composite.

24. The reinforced networked polymer/clay alloy composite of claim 23, wherein the reinforcing agent comprises a substrate having a porous structure.

25. The reinforced networked polymer/clay alloy composite of claim 24, wherein the substrate is selected from the group consisting of knitted, woven and non-woven, natural and synthetic fibers.

26. The reinforced networked polymer/clay alloy composite of claim 25, wherein the synthetic fibers are selected from the group consisting of polypropylene, polyester, polyamide, polyethylene fibers, and combinations thereof.

27. The reinforced networked polymer/clay alloy composite of claim 23, wherein the clay particles in the alloy are swelling clay particles selected from the group consisting of montmorillonite, saponite, nontronite, laponite, beidellite, iron-saponite, hectorite, sauconite, stevensite, vermiculite and combinations thereof.

28. The reinforced networked polymer/clay alloy composite of claim 23, wherein the clay particles in the alloy are non-swelling clay particles selected from the group consisting of kaolin minerals, serpentine minerals, mica minerals, chlorite minerals, sepiolite, palygorskite, bauxite, silica and combinations thereof.

29. The reinforced networked polymer/clay alloy composite of claim 23, wherein the weight ratio of clay to polymer in the alloy is in a range of from about 0.05:1 to about 19:1.

30. The reinforced networked polymer/clay alloy composite of claim 23, wherein the weight ratio of clay to polymer in the alloy is in a range of from about 0.5:1 to about 3:1.

31. The reinforced networked polymer/clay alloy composite of claim 23, wherein the polymer of the alloy is a copolymer of a water-insoluble monomer and a monomer having the following general formula:

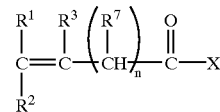

wherein X is selected from the group consisting of OM, $OR^4$ and $NR^5R^6$, M is an alkali or alkaline earth metal ion or $NH_4^+$, $R^1$, $R^2$, $R^3$, $R^5$, $R^6$ and $R^7$ are independently selected from the group consisting of H, $CH_3$, $CH_2CH_3$, $CH_2CH_2CH_3$, $CH(CH_3)_2$, $CH_2CH_2CH_2CH_3$, and CN, and $OR^4$ is selected from the group consisting of OH, $OCH_3$, $OCH_2CH_3$, $OCH_2CH_2CH_3$, $OCH(CH_3)_2$, $OCH_2CH_2CH_2CH_3$, $OCH_2CH_2OH$ and $(OCH_2CH_2)_mOH$, n=0 to about 10 and m=1 to about 10.

32. The reinforced networked polymer/clay alloy composite of claim 23, wherein the alloy is formed by exposure to an energy source selected from the group consisting of thermal energy, electromagnetic radiation having a wavelength less than about 10 nm and combinations thereof.

33. The reinforced networked polymer/clay alloy composite of claim 23, further comprising a substantially non-porous layer.

34. The reinforced networked polymer/clay alloy composite of claim 33, wherein the substantially non-porous layer is selected from the group consisting of HDPE, PVC, VFPE, fPP, CSPE, and combinations thereof.

35. The reinforced networked polymer/clay alloy composite of claim 23, wherein the moisture content is in a range of from about 25 to about 75% by weight.

36. The reinforced networked polymer/clay alloy composite of claim 23, wherein the residual monomer content is less than 200 ppm by weight of the polymer in the alloy.

37. The reinforced networked polymer/clay alloy composite of claim 23, wherein, when placed under a zero confining stress, the flux with deionized water is less than about $1 \times 10^{-8}$ $m^3/m^2/s$.

38. The reinforced networked polymer/clay alloy composite of claim 23, wherein, when placed under a zero confining stress, the flux with a 3.5 wt. % NaCl solution is less than about $1 \times 10^{-8}$ $m^3/m^2/s$.

39. The method of using the reinforced networked polymer/clay alloy composite of claim 23 as a fluid barrier in a confining stress range of from about 0 kPa to about 10000 kPa, wherein, when placed under a zero confining stress, the barrier has a deionized water flux less than about $1 \times 10^{-8}$ $m^3/m^2/s$.

40. The method of using the reinforced networked polymer/clay alloy composite of claim 23 as an absorbent material used in a personal care article.

41. A reinforced networked polymer/clay alloy composite produced by the process of claim 2, comprising a networked polymer/clay alloy, wherein the alloy is a chemically integrated composition of polymer and clay, and the alloy is intimately integrated with a reinforcing agent so that, when the composite is immersed in deionized water, at a temperature in a range of from about 20° C. to about 30° C., the alloy swells with substantially no clay separating from the composite.

42. The reinforced networked polymer/clay alloy composite of claim 41, wherein the substrate is selected from the group consisting of knitted, woven and non-woven, natural and synthetic fibers.

43. The reinforced networked polymer/clay alloy composite of claim 42, wherein the synthetic fibers are selected from the group consisting of polypropylene, polyester, polyamide, polyethylene fibers, and combinations thereof.

44. The reinforced networked polymer/clay alloy composite of claim 41, wherein the clay particles in the alloy are swelling clay particles selected from the group consisting of montmorillonite, saponite, nontronite, laponite, beidellite, iron-saponite, hectorite, sauconite, stevensite, vermiculite and combinations thereof.

45. The reinforced networked polymer/clay alloy composite of claim 41, wherein the clay particles in the alloy are non-swelling clay particles selected from the group consisting of kaolin minerals, serpentine minerals, mica minerals, chlorite minerals, sepiolite, palygorskite, bauxite, silica and combinations thereof.

46. The reinforced networked polymer/clay alloy composite of claim 41, wherein the weight ratio of clay to polymer in the alloy is in a range of from about 0.05:1 to about 19:1.

47. The reinforced networked polymer/clay alloy composite of claim 41, wherein the weight ratio of clay to polymer in the alloy is in a range of from about 0.5:1 to about 3:1.

48. The reinforced networked polymer/clay alloy composite of claim 41, wherein the polymer of the alloy is a copolymer of a water-insoluble monomer and a monomer having the following general formula:

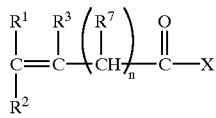

wherein X is selected from the group consisting of OM, $OR^4$ and $NR^5R^6$, M is an alkali or alkaline earth metal ion or $NH_4^+$, $R^1$, $R^2$, $R^3$, $R^5$, $R^6$ and $R^7$ are independently selected from the group consisting of H, $CH_3$, $CH_2CH_3$, $CH_2CH_2CH_3$, $CH(CH_3)_2$, $CH_2CH_2CH_2CH_3$, and CN, and $OR^4$ is selected from the group consisting of OH, $OCH_3$, $OCH_2CH_3$, $OCH_2CH_2CH_3$, $OCH(CH_3)_2$, $OCH_2CH_2CH_2CH_3$, $OCH_2CH_2OH$ and $(OCH_2CH_2)_mOH$, n=0 to about 10 and m=1 to about 10.

49. The reinforced networked polymer/clay alloy composite of claim 41, wherein the alloy is formed by exposure to an energy source selected from the group consisting of thermal energy, electromagnetic radiation having a wavelength less than about 10 nm and combinations thereof.

50. The reinforced networked polymer/clay alloy composite of claim 41, further comprising a substantially non-porous layer.

51. The reinforced networked polymer/clay alloy composite of claim 50, wherein the substantially non-porous layer is selected from the group consisting of HDPE, PVC, VFPE, fPP, CSPE, and combinations thereof.

52. The reinforced networked polymer/clay alloy composite of claim 41, wherein the moisture content is in a range of from about 25 to about 75% by weight.

53. The reinforced networked polymer/clay alloy composite of claim 41, wherein the residual monomer content is less than 200 ppm by weight of the polymer in the alloy.

54. The reinforced networked polymer/clay alloy composite of claim 41, wherein, when placed under a zero confining stress, the flux with deionized water is less than about $1 \times 10^{-8}$ $m^3/m^2/s$.

55. The reinforced networked polymer/clay alloy composite of claim 41, wherein, when placed under a zero confining stress, the flux with a 3.5 wt. % NaCl solution is less than about $1 \times 10^{-8}$ $m^3/m^2/s$.

56. The method of using the reinforced networked polymer/clay alloy composite of claim 41 as a fluid barrier in a confining stress range of from about 0 kPa to about 10000 kPa, wherein, when placed under a zero confining stress, the barrier has a deionized water flux less than about $1 \times 10^{-8}$ $m^3/m^2/s$.

57. The method of using the reinforced networked polymer/clay alloy composite of claim 41 as an absorbent material used in a personal care article.

* * * * *